United States Patent
Nabatame et al.

(10) Patent No.: US 9,477,880 B2
(45) Date of Patent: Oct. 25, 2016

(54) BEHAVIOR DETECTION METHOD AND BEHAVIOR DETECTION APPARATUS

(71) Applicant: FUJITSU LIMITED, Kawasaki-shi, Kanagawa (JP)

(72) Inventors: Shinya Nabatame, Setagaya (JP); Kimitaka Murashita, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/056,039

(22) Filed: Feb. 29, 2016

(65) Prior Publication Data

US 2016/0259969 A1    Sep. 8, 2016

(30) Foreign Application Priority Data

Mar. 3, 2015   (JP) ................................ 2015-041791

(51) Int. Cl.
G06K 9/00       (2006.01)

(52) U.S. Cl.
CPC ....... *G06K 9/00335* (2013.01); *G06K 9/00362* (2013.01)

(58) Field of Classification Search
None
See application file for complete search history.

(56) References Cited

U.S. PATENT DOCUMENTS

2013/0215248 A1*  8/2013  Ishii ..................... A61B 5/1113
                                                                348/77

FOREIGN PATENT DOCUMENTS

| JP | 2012-71003 | 4/2012 |
| JP | 2012-170483 | 9/2012 |
| JP | 2013-149205 | 8/2013 |

* cited by examiner

*Primary Examiner* — Siamak Harandi
*Assistant Examiner* — Amandeep Saini
(74) *Attorney, Agent, or Firm* — Staas & Halsey LLP

(57) ABSTRACT

A behavior detection apparatus detects a position of a head from an image; based on the position of the head, detects a motion of bending forward when a person to be detected sits up in a width direction of a bed in a bed area of the image and stands up from the sitting state; when a movement of the head is detected to be forward bending, sets, based on a movement path of the head, a stand-up detection line for determining bed leaving of the person between a lowest point of the forward bending and the position of the head when the person stands by the bed, the stand-up detection line being set in a position not overlapping with a forward bending detection line by which the motion of bending forward is detected; and detects a stand-up motion when the head passes the set stand-up detection line.

5 Claims, 23 Drawing Sheets

FIG.6

| BED | | HEIGHT | B1 | mm |
|---|---|---|---|---|
| | | HALF WIDTH | B2 | mm |
| PATIENT | PHYSICAL SIZE | HEAD HEIGHT | H1 | mm |
| | | HEAD LENGTH | H2 | mm |
| | | THIGH LENGH | H3 | mm |
| | | DISTANCE FROM BED END TO FEET | H4 | mm |
| | | SITTING HEIGHT | H5 | mm |
| | | HEIGHT | H6 | mm |
| | MOTION | FORWARD TILT ANGLE OF TRUNK WHEN STANDING UP | H7 | deg |
| | | AMOUNT OF FORWARD MOVEMENT WHEN STANDING UP | H8 | mm |

FIG.22

| PARAMETER SETTING | | | PATH 1 | PATH 2 | PATH DEFAULT |
| --- | --- | --- | --- | --- | --- |
| | DESCRIPTION | SYMBOL | UNIT | | | |
| MOTION | FORWARD TILT ANGLE OF TRUNK WHEN STANDING UP | H7 | deg | 20 (MINIMUM) | 60 (MAXIMUM) | 40 (AVERAGE) |
| | POSITION WHEN STANDING BY BED | H8 | mm | 0 (MINIMUM) | 300 (MAXIMUM) | 150 (AVERAGE) |
| | DIRECTION OF STAND-UP MOTION | $\theta$ | deg | -45 (MINIMUM) | 45 (MAXIMUM) | 0 (AVERAGE) |

FIG.23

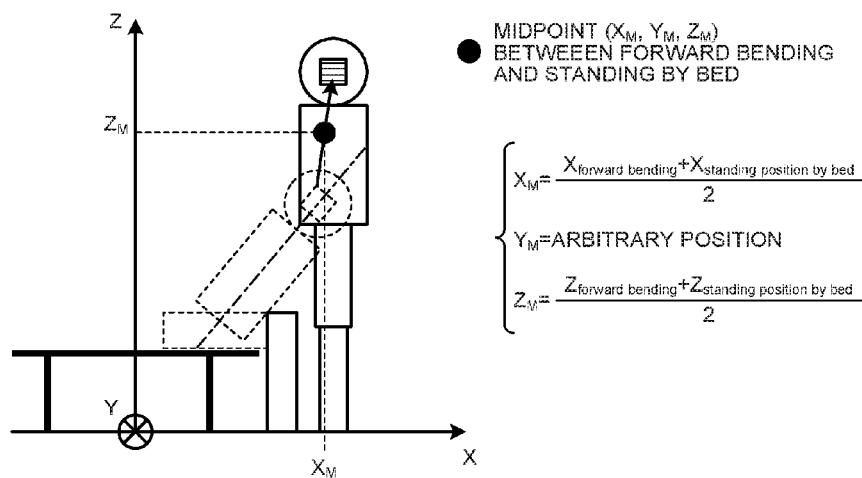

● MIDPOINT $(X_M, Y_M, Z_M)$ BETWEEEN FORWARD BENDING AND STANDING BY BED $$\begin{cases} X_M = \dfrac{X_{\text{forward bending}} + X_{\text{standing position by bed}}}{2} \\ Y_M = \text{ARBITRARY POSITION} \\ Z_M = \dfrac{Z_{\text{forward bending}} + Z_{\text{standing position by bed}}}{2} \end{cases}$$

FIG.25
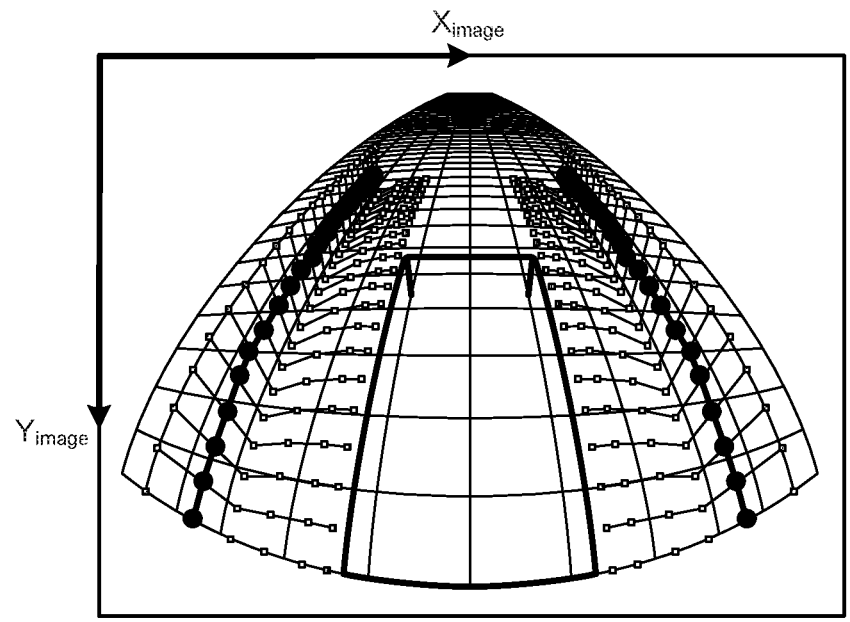
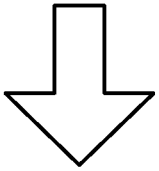
CONNECT ADJOINING POINTS
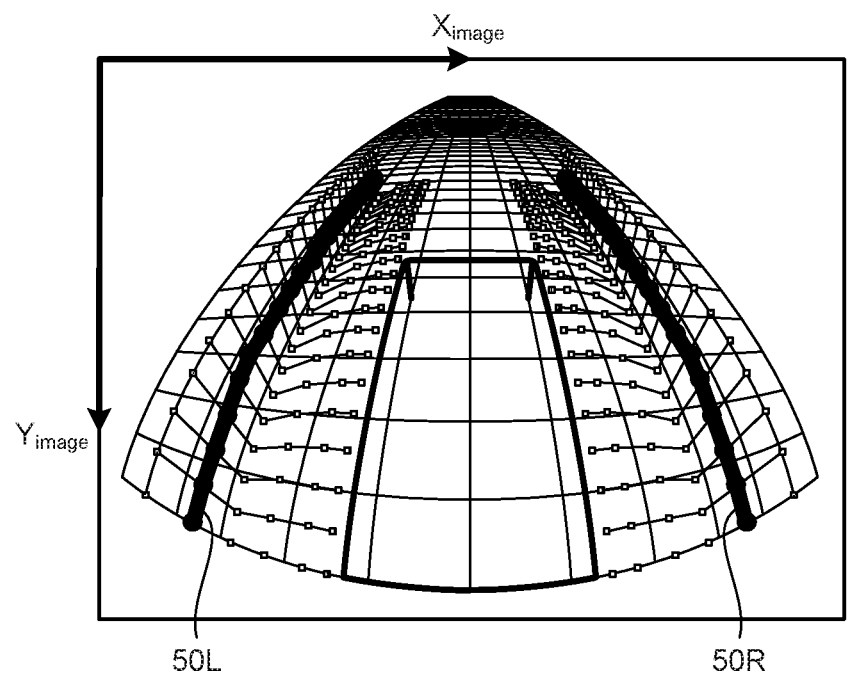

BEHAVIOR DETECTION METHOD AND BEHAVIOR DETECTION APPARATUS

CROSS-REFERENCE TO RELATED APPLICATION

This application is based upon and claims the benefit of priority of the prior Japanese Patent Application No. 2015-041791, filed on Mar. 3, 2015, the entire contents of which are incorporated herein by reference.

FIELD

The embodiments discussed herein are directed to a behavior detection method and a behavior detection apparatus.

BACKGROUND

In medical and nursing care facilities, accidents such as wandering and a fall can occur when a patient leaves his/her bed without being noticed by caregivers. To suppress the occurrence of such accidents, a technique for detecting a motion related to the leaving of a patient from a bed, such as standing up, has been proposed.

For example, a camera for capturing a head of a patient or the like is installed above the head side of the bed, like directly above the headboard. The bed leaving of the patient or the like is detected depending on whether the position of the head detected from an image captured by the camera exceeds lines that are set with reference to both sides of the bed.

Patent document 1: Japanese Laid-open Patent Publication No. 2012-170483

Patent document 2: Japanese Laid-open Patent Publication No. 2013-149205

Since a camera installed above the head side of the bed may interfere with treatment or caregiving, a camera is not always able to be installed above the head side of the bed. If a camera is installed in an oblique direction to the bed and the lines for determining the leaving from the bed are set with reference to both sides of the bed, the lines to be used to determine the bed leaving may be set in an area where the bed appears in the image captured by the camera. In such a case, the head can pass the lines due to a motion made on the bed other than standing up, like a roll-over and a motion in a sitting position. This causes false detection of the bed leaving.

SUMMARY

According to an aspect of an embodiment, a behavior detection method includes: detecting a position of a head from an image; detecting, based on the position of the head, a motion of bending forward when a person to be detected sits up in a width direction of a bed in a bed area of the image and stands up from the sitting state; when a movement of the head is detected to be forward bending, dynamically setting, based on a movement path of the head, a stand-up detection line for determining bed leaving of the person to be detected between a lowest point of the forward bending and the position of the head when the person to be detected stands by the bed, the stand-up detection line being set in a position not overlapping with a forward bending detection line by which the motion of bending forward is detected; and detecting a stand-up motion when the head passes the dynamically set stand-up detection line.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 6 is a diagram illustrating an example of first parameters;

FIG. 22 is a diagram illustrating an application example of settings of motion-related parameters;

FIG. 23 is a diagram illustrating an example of a stand-up intermediate point;

FIG. 25 is a diagram illustrating an example of the method for setting stand-up lines.

DESCRIPTION OF EMBODIMENTS

Preferred embodiments will be explained with reference to accompanying drawings. Note that the following embodiments are not intended to limit the technique of the disclosure. The embodiments may be combined as appropriate without a conflict between the processing contents.

[a] First Embodiment

Configuration of Behavior Detection System

Figure 1:
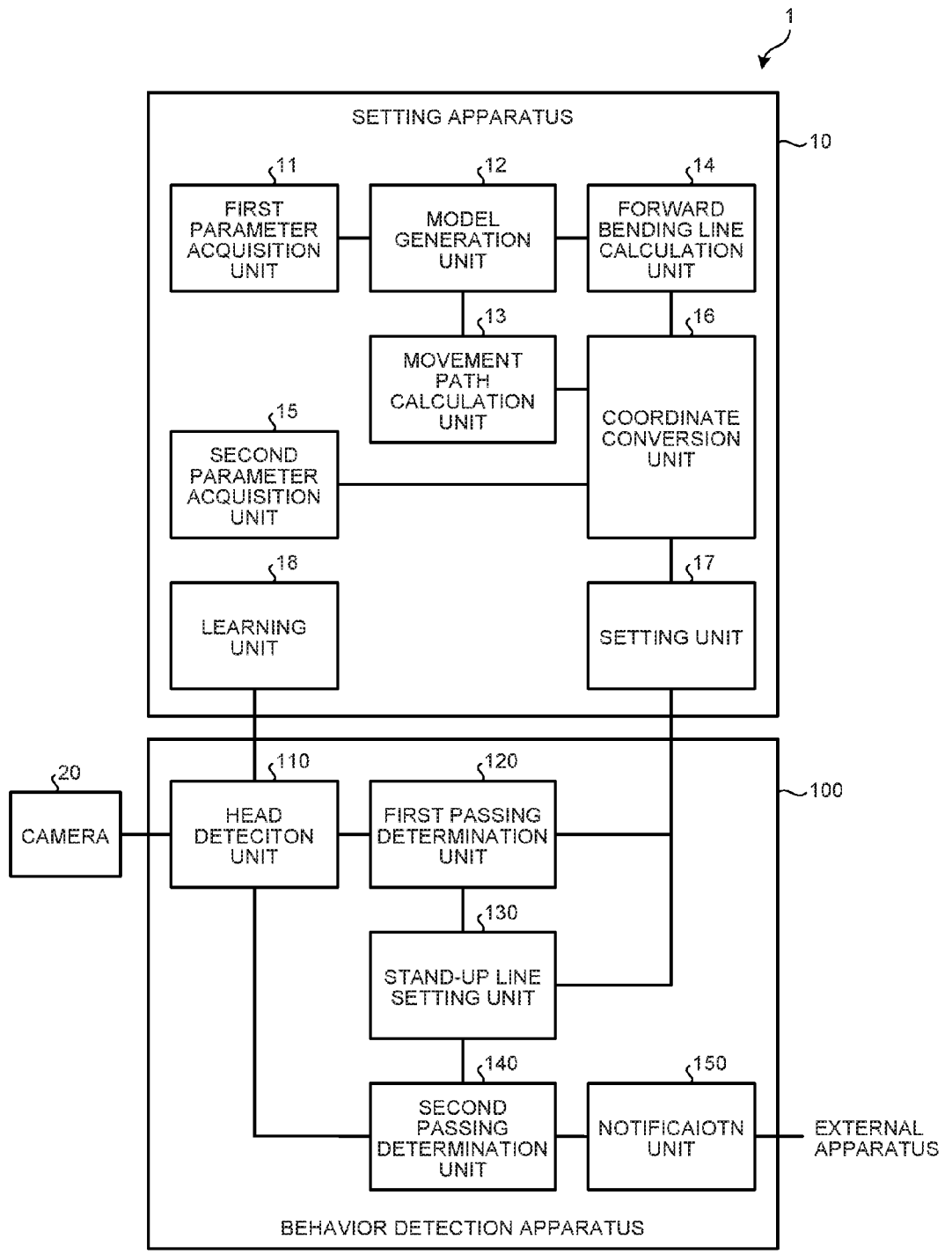
FIG. 1 is a block diagram illustrating a functional configuration of apparatuses included in a behavior detection system according to a first embodiment.

FIG. 1 is a block diagram illustrating a functional configuration of apparatuses included in a behavior detection system according to a first embodiment. A behavior detection system 1 illustrated in FIG. 1 is applicable to medical and nursing care facilities. Using an image captured by a camera 20, the behavior detection system 1 provides a service for detecting a motion related to the behavior of a user of a bed, such as a patient and a person who is in need of nursing care, leaving the bed, for example, standing up.

As part of such a behavior detection service, the behavior detection system 1 dynamically sets a line for determining bed leaving according to a head's movement path predicted when the user stands up from a forward bending posture detected from the image captured by the camera 20, and determines whether the head passes the line.

Consequently, even if the line used to determine the bed leaving is set in an area where the bed appears in the image captured by the camera 20, the occurrence of false detection of the bed leaving due to motions made on the bed other than standing up, such as a roll-over and a motion in a sitting position, can be suppressed. As a result, the flexibility of an installation position of the camera 20 used for the detection of the bed leaving can be increased.

In the following description, a line for determining forward bending from the passing of the head on the image may be referred to as a "forward bending line." The line for determining the bed leaving, e.g., standing up from the passing of the head on the image may be referred to as a stand-up line.

As illustrated in FIG. 1, the behavior detection system 1 includes a setting apparatus 10, the camera 20, and a behavior detection apparatus 100. While FIG. 1 illustrates a single camera 20, the behavior detection system 1 may include a plurality of cameras 20.

The setting apparatus 10 and the behavior detection apparatus 100 are communicably connected via a predetermined network, and so are the camera 20 and the behavior detection apparatus 100. Examples of such a network may include arbitrary types of wired and wireless communication networks such as the Internet, a local area network (LAN), and a virtual private network (VPN).

The setting apparatus 10 is an apparatus for making various settings about the behavior detection apparatus 100.

In one embodiment, the setting apparatus 10 may be implemented as an information processing apparatus to be used by a person concerned of the facility. For example, a desktop or notebook personal computer may be employed as the setting apparatus 10. Other examples applicable to the setting apparatus 10 may include mobile communication terminals such as a smartphone, a mobile phone, and a Personal Handyphone System (PHS), and slate terminals such as personal digital assistants (PDAs). The setting apparatus 10 may be implemented as a console of the behavior detection apparatus 100.

For example, the setting apparatus 10 sets, with respect to the behavior detection apparatus 100, forward bending lines which the behavior detection apparatus 100 uses when detecting the foregoing forward bending posture. The setting apparatus 10 also sets, with respect to the behavior detection apparatus 100, predicted lines of head movement paths which the behavior detection apparatus 100 uses when setting the foregoing stand-up lines, i.e., movement paths predicted when the head moves from the forward bending posture to a standing position along a physiological curve. The setting apparatus 10 further generates an identifier which the behavior detection apparatus 100 uses to detect the head of the user of the bed from an image captured by the camera 20.

FIG. 1 illustrates a case where the setting apparatus 10 makes various settings about the behavior detection apparatus 100. However, if the forward bending lines, the predicted lines of the head movement paths, and the identifier for head detection are set in the behavior detection apparatus 100, the foregoing behavior detection service may be performed without using the setting apparatus 10. The setting apparatus 10 and the behavior detection apparatus 100 need not necessarily be configured as separate members. The behavior detection apparatus 100 may include the functions of the setting apparatus 10.

The camera 20 is an imaging apparatus including an imaging sensor such as a charge coupled device (CCD) image sensor and a complementary metal oxide semiconductor (CMOS) image sensor.

In one embodiment, the camera 20 may include three or more types of light receiving elements like red (R), green (G), and blue (B) light receiving elements. However, the image does not necessarily need to include color information, and may be in gray scale. Gradation values of the image are not limited to those of the RGB color system. For example, the gradation values may be expressed by the HSV (hue, saturation, value) color system, the YUV color system, or the like.

The camera 20 is installed in a position where all or part of a patient bed provided in the medical or nursing care facility is captured within its imaging range. For example, the camera 20 can be installed at a height where the side ends of the top surface (bed surface) of the bed can be captured while being directed in a direction from the head side to the foot side of the bed. If the camera 20 is installed in such a manner, the camera 20 need not necessarily be installed in a position above the head side of the bed, for example, directly above the headboard. For example, the camera 20 may be arranged to be horizontally shifted from above the head side of the bed in the bed's width direction which is an X-axis direction to be described later with reference to FIG. 2. In the following description, the camera 20 is assumed to be installed to be directed in a direction from the head side to the foot side of the bed. However, the camera 20 may be installed to be directed in a direction from the foot side to the head side of the bed.

The behavior detection apparatus 100 is a computer that provides the foregoing behavior detection service.

In one embodiment, the behavior detection apparatus 100 can be implemented by installing a behavior detection program for achieving the foregoing behavior detection service in a desired computer in the form of package software or online software. For example, the behavior detection apparatus 100 may be implemented as a web server that provides the foregoing behavior detection service. The behavior detection apparatus 100 may be implemented as a cloud for providing the foregoing behavior detection service by outsourcing.

Coordinate Systems

The forward bending lines and the predicted lines of the head movement paths described above are data in an image coordinate system that is set on the image captured by the camera 20. The data is a projection of coordinates defined in the three-dimensional space of the environment where the camera 20 is installed, onto a two-dimensional image coordinate system. For example, a ground coordinate system is defined as the coordinate system of the three-dimensional space. If the coordinates in the ground coordinate system are projected onto coordinates in the image coordinate system, a camera coordinate system of the camera 20 is used.

Figure 2:
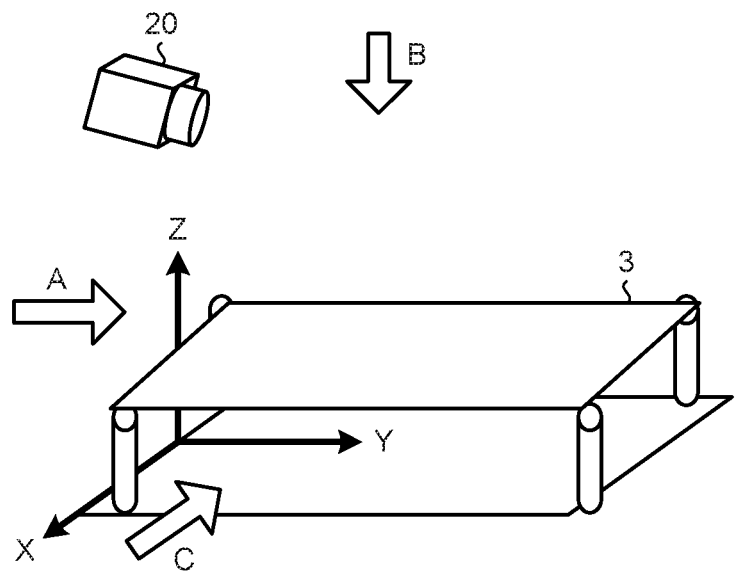
FIG. 2 is a diagram illustrating a ground coordinate system.
Figure 3:
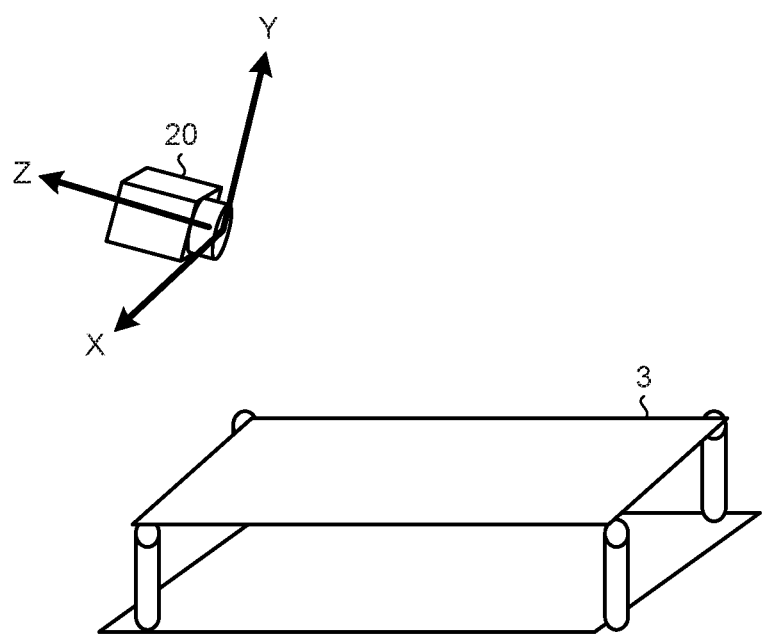
FIG. 3 is a diagram illustrating an example of a camera coordinate system.
Figure 4A:
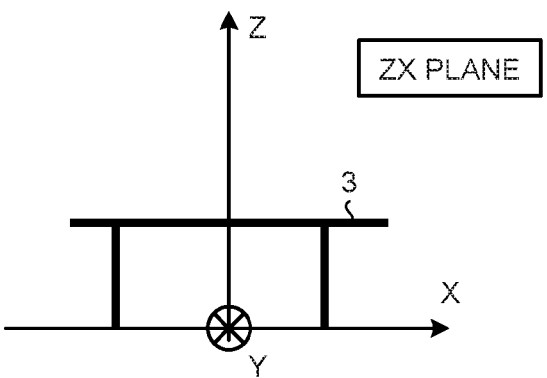
FIG. 4A is a diagram illustrating an example of a view of the ground coordinate system.
Figure 4B:
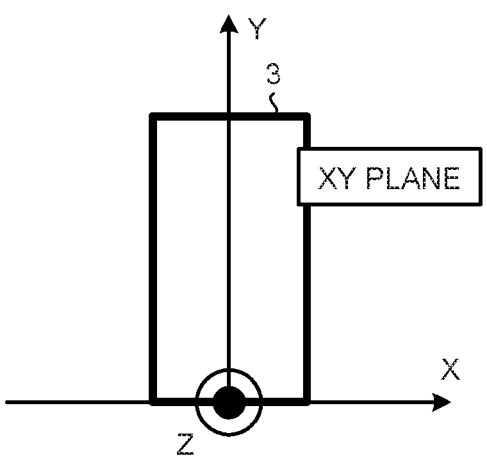
FIG. 4B is a diagram illustrating an example of a view of the ground coordinate system.
Figure 4C:
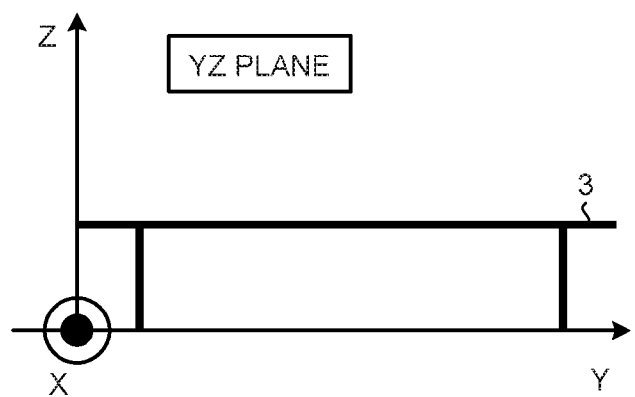
FIG. 4C is a diagram illustrating an example of a view of the ground coordinate system.
Figure 5A:
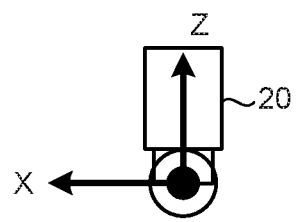
FIG. 5A is a diagram illustrating an example of an orthogonal plane of the camera coordinate system.
Figure 5B:
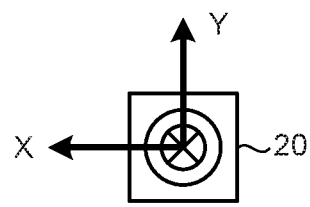
FIG. 5B is a diagram illustrating an example of an orthogonal plane of the camera coordinate system.
Figure 5C:
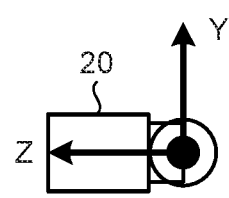
FIG. 5C is a diagram illustrating an example of an orthogonal plane of the camera coordinate system.

Now, the ground coordinate system and the camera coordinate system according to the present embodiment will be described with reference to FIGS. 2 to 5C. FIG. 2 is a diagram illustrating an example of the ground coordinate system. FIG. 3 is a diagram illustrating an example of the camera coordinate system. FIGS. 4A to 4C are diagrams illustrating examples of views of the ground coordinate system. FIGS. 5A to 5C are diagrams illustrating examples of orthogonal planes of the camera coordinate system.

As illustrated in FIG. 2, the ground coordinate system is a coordinate system with a point directly below the center of a side on the head side of a bed surface of a bed 3 as the origin of the three-dimensional space. The width direction of the bed 3 is assumed to be the X-axis, the depth direction of the bed 3 the Y-axis, and the height direction of the bed 3 the Z-axis. FIG. 4A illustrates a projection of the ground coordinate system illustrated in FIG. 2 onto the ZX plane, seen in the direction of the arrow A. FIG. 4B illustrates a projection onto the XY plane, seen in the direction of the arrow B. FIG. 4C illustrates a projection onto the YZ plane, seen in the direction of the arrow C. As illustrated in FIG. 3, the camera coordinate system is a coordinate system with respect to the camera 20 illustrated in FIG. 1. A lens focus of the camera 20 is assumed to be the origin of the three-dimensional space. FIG. 5A illustrates a projection of the camera coordinate system illustrated in FIG. 3 onto the ZX plane. FIG. 5B illustrates a projection onto the XY plane. FIG. 5C illustrates a projection on the YZ plane.

Configuration of Setting Apparatus 10

Next, a functional configuration of the setting apparatus 10 according to the present embodiment will be described. As illustrated in FIG. 1, the setting apparatus 10 includes a first parameter acquisition unit 11, a model generation unit 12, a movement path calculation unit 13, a forward bending line calculation unit 14, a second parameter acquisition unit 15, a coordinate conversion unit 16, a setting unit 17, and a learning unit 18.

The first parameter acquisition unit 11 is a processing unit that obtains first parameters.

As employed herein, the "first parameters" refer to parameters about the bed 3 and its user. Details will be described later with reference to FIG. 7. Examples of the items include those listed in FIG. 6. FIG. 6 is a diagram illustrating examples of the first parameters. For example, FIG. 6 illustrates first parameters in a case where the user of the bed 3 is a patient hospitalized in a facility such as a hospital. As illustrated in FIG. 6, the parameters about the bed 3 include items such as a height B1 of the bed 3 and a half width B2 of the bed 3. The parameters about the patient can be divided into ones about physical sizes and ones about motions. The parameters about physical sizes include a head height H3, a head length H2, and a thigh length H3 of the patient, a distance H4 from a side end in the width direction of the bed 3 to a landing area of the feet in an end seating position, a sitting height H5, a height H6, etc. The parameters about motions include an angle H7 at which the trunk of the patient tilts forward when the patient takes a forward bending posture as a preliminary motion of standing up, the amount of forward movement H8 by which the landing area of the patient's feet moves forward in the width direction of the bed 3 as the posture changes from the end seating position to a standing position, etc. The "end seating position" refers to a posture in which the patient is seated on the left or right end of the bed 3 with the feet down toward the width direction of the bed.

In one embodiment, the first parameter acquisition unit 11 can obtain the foregoing first parameters by input operations via a not-illustrated input device. The first parameter acquisition unit 11 can also obtain the first parameters from an auxiliary storage device such as a hard disk and an optical disk, or a removable medium such as a memory card and a Universal Serial Bus (USB) memory. The first parameter acquisition unit 11 can further receive and obtain the first parameters from an external apparatus via a network.

The model generation unit 12 is a processing unit that generates a stand-up model of the patient by using the foregoing first parameters. As employed herein, the "stand-up model" refers to a schematic model of the motion of the patient standing up from the bed 3.

Figure 7:
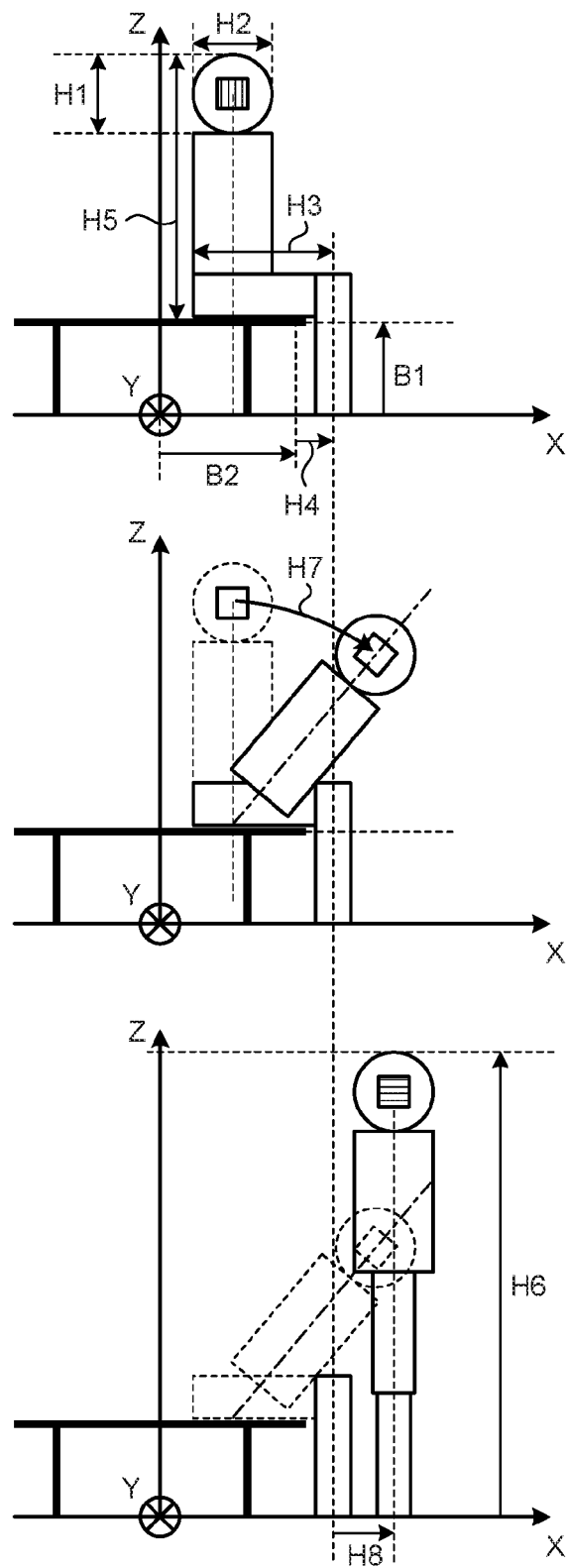
FIG. 7 is a diagram illustrating an example of a stand-up model.

In one embodiment, the model generation unit 12 virtually reproduces a model of the patient in the ground coordinate system under a condition setting such that the posture of the patient changes in order of the end seating position with his/her back toward an end of the bed 3, forward bending in the end seating state, and a standing position by the bed 3. FIG. 7 is a diagram illustrating an example of the stand-up model. The top part of FIG. 7 illustrates the model of the patient in the end seating position. The middle part of FIG. 7 illustrates the model of the patient bending forward. The bottom part of FIG. 7 illustrates the model of the patient in the standing position. As illustrated in FIG. 7, the model generation unit 12 can reproduce the stand-up model of the patient on the XZ plane according to the first parameters obtained by the first parameter acquisition unit 11. In other words, the model generation unit 12 can set the model of the patient in an arbitrary Y coordinate where the bed 3 exists. FIG. 7 illustrates the case where the patient is seated on the right end of the bed 3 as seen in the direction of the arrow A illustrated in FIG. 2. A similar stand-up model can also be reproduced if the patient is seated on the left end of the bed 3.

The movement path calculation unit 13 is a processing unit that calculates the head movement paths of the foregoing stand-up model.

Figure 8:
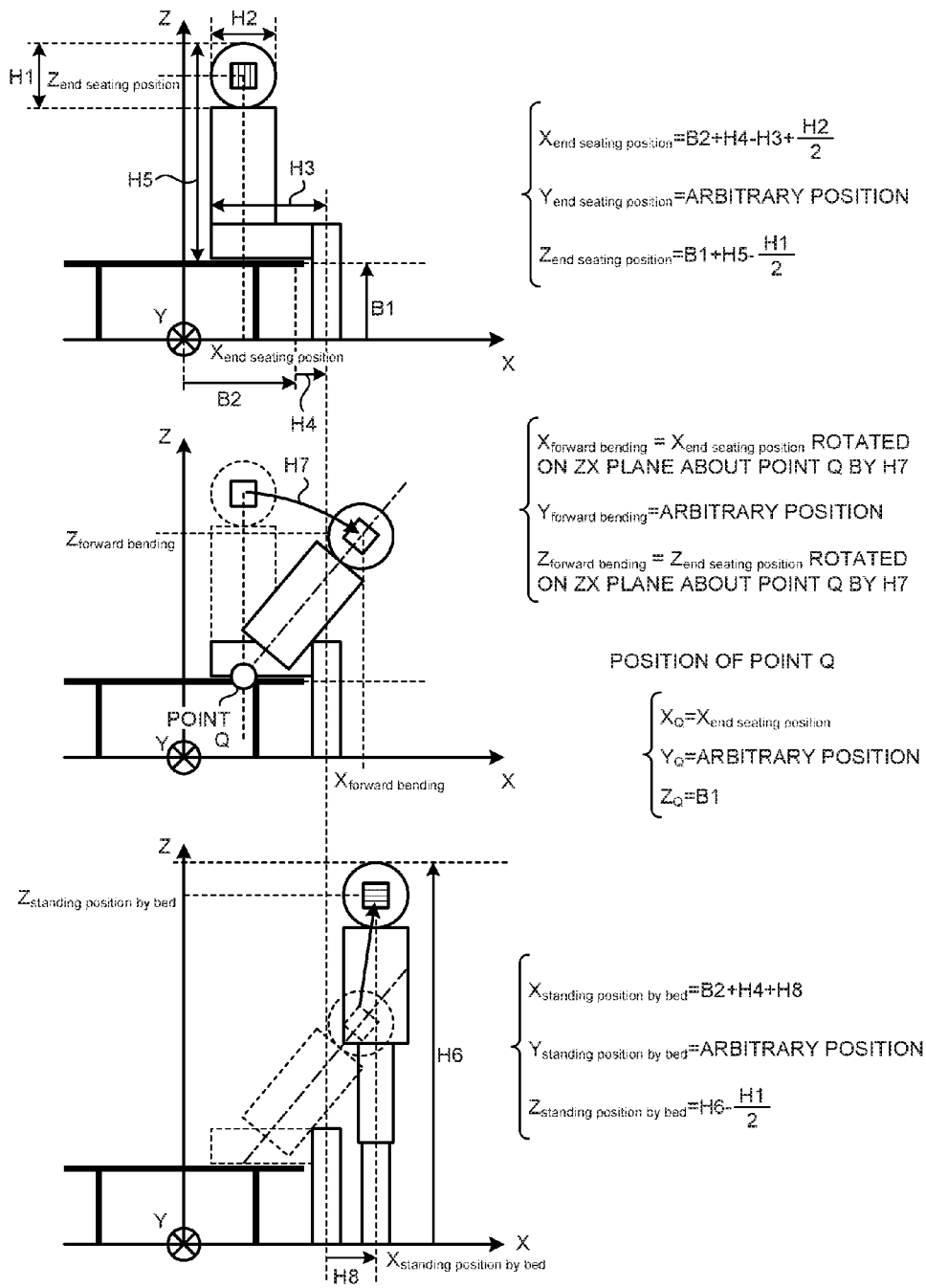
FIG. 8 is a diagram illustrating an example of a head movement path.

In one embodiment, the movement path calculation unit 13 calculates the position of the head in each of the postures included in the stand-up model generated by the model generation unit 12. FIG. 8 is a diagram illustrating an example of the head movement path. FIG. 8 illustrates the stand-up model illustrated in FIG. 7 in order of the end seating position, the forward bending, and the standing position from above. As illustrated in FIG. 8, the movement path calculation unit 13 calculates the position of the head in each of the three postures, i.e., the end seating position, the forward bending, and the standing position. For example, assuming that the head is circular in shape, the movement path calculation unit 13 calculates coordinates ($X_{end\ seating\ position}$, $Y_{end\ seating\ position}$, $Z_{end\ seating\ position}$) of the center of the head in the ground coordinate system.

For example, the head in the end seating position is located in the position of the rectangle that is illustrated as being filled with vertical lines in FIG. 8. $X_{end\ seating\ position}$ can be determined by using the half width B2 of the bed 3, the head length H2, the thigh length H3, and the distance H4 among the first parameters. More specifically, the movement path calculation unit 13 calculates the position $X_{end\ seating\ position}$ of the head in the end seating position by calculating "B2+H4−H3+H2/2." $Z_{end\ seating\ position}$ can be determined by using the height B1 of the bed 3, the head height H1, and the sitting height H5 among the first parameters. More specifically, the movement path calculation unit 13 calculates the position $Z_{end\ seating\ position}$ of the head in the end seating position by calculating "B1+H5−H1/2." The position $Y_{end\ seating\ position}$ of the head in the end seating position may be an arbitrary Y coordinate that can be projected onto the bed surface of the bed 3 by projection in the Z-axis direction.

The head in the forward bending is located in the position of the rectangle that is illustrated as being filled with white in FIG. 8. Suppose that the coordinates ($X_Q$, $Y_Q$, $Z_Q$) of a center Q about which the trunk of the patient rotates are ($X_{end\ seating\ position}$, an arbitrary coordinate, B1). Then, $X_{forward\ bending}$ can be determined by rotating $X_{end\ seating\ position}$ on the ZX plane about the point Q by the forward tilt angle H7 of the trunk. Similarly, $Z_{forward\ bending}$ can be determined by rotating $Z_{end\ seating\ position}$ on the ZX plane about the point Q by the forward tilt angle H7 of the trunk.

The head in the standing position is located in the position of the rectangle that is illustrated as being filled with horizontal lines in FIG. 8. $X_{standing\ position\ by\ bed}$ can be determined by using the half width B2 of the bed 3, the distance H4, and the amount of forward movement H8 among the first parameters. More specifically, the movement path calculation unit 13 calculates the position $X_{standing\ position\ by\ bed}$ of the head in the standing position by calculating "B2+H4+H8." $Z_{standing\ position\ by\ bed}$ can be determined by using the head height H1 and the height H6 among the first parameters. More specifically, the movement path calculation unit 13 calculates the position $Z_{standing\ position\ by\ bed}$ of the head in the standing position by calculating "H6−H1/2."

By calculating the positions of the head in the three postures, the end seating position, the forward bending, and the standing position, the movement path calculation unit 13 can determine a head moving path to be a movement path having the position of the head in the end seating position as a starting point, the position of the head in the forward bending as a transit point, and the position of the head in the standing position as an end point. Such head movement paths are separately calculated for the case where the patient takes the end seating position on the left end of the bed 3 and for the case where the patent takes the end seating position on the right end of the bed 3. The head movement paths are further calculated at pitches with which the Y coordinates where the bed 3 exists in the three-dimensional space of the ground coordinate system are sectioned at regular intervals, such as in units of 10 cm, in the depth direction of the bed 3.

The forward bending line calculation unit 14 is a processing unit that calculates the foregoing forward bending line.

Figure 9:
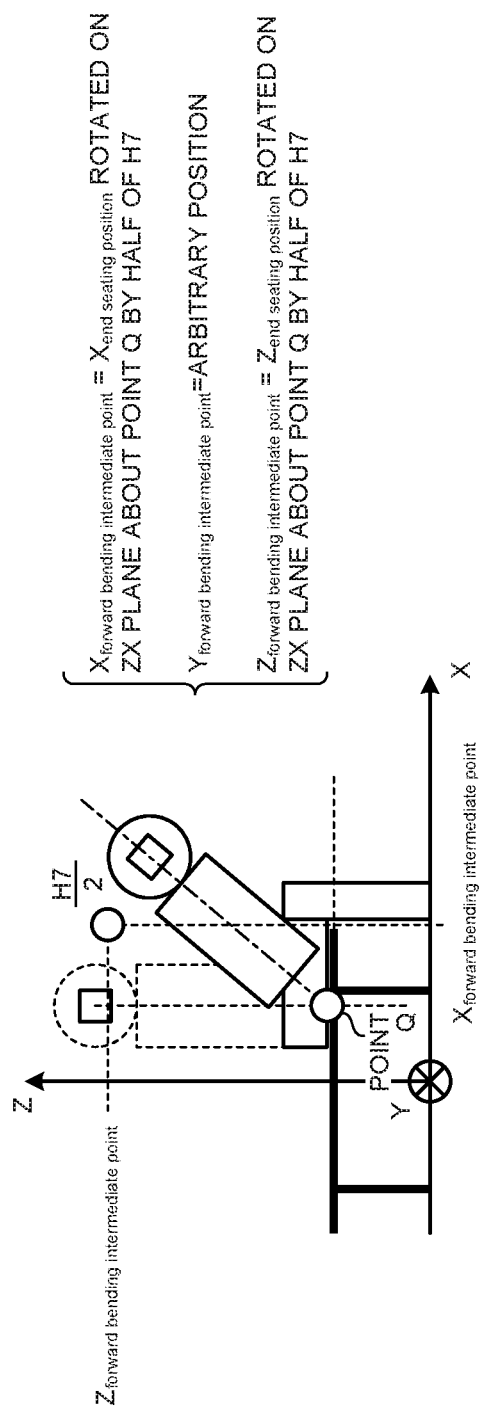
FIG. 9 is a diagram illustrating an example of a forward bending intermediate point.

In one embodiment, the forward bending line calculation unit 14 determines the position of the head in an arbitrary intermediate point on the movement path along which the head of the patient moves from the end seating position to the forward bending in the stand-up model. For example, a case of determining the position of the head at a midpoint of the movement path along which the head of the patient moves from the end seating position to the forward bending will be described. The midpoint of the movement path along which the head of the patient moves from the end seating position to the forward bending may hereinafter be referred to as a "forward bending intermediate point." FIG. 9 is diagram illustrating an example of the forward bending intermediate point. In FIG. 9, the model of the patient in the end seating position is illustrated by broken lines. The model of the patient bending forward is illustrated by solid lines. As illustrated in FIG. 9, the head at the forward bending intermediate point is located in the position of the circle that is illustrated as being filled with white in FIG. 9. Suppose that the coordinates ($X_Q$, $Y_Q$, $Z_Q$) of the center Q about which the trunk of the patient rotates are ($X_{end\ seating\ position}$, an arbitrary coordinate, B1). Then, $X_{forward\ bending\ intermediate\ point}$ can be determined by rotating $X_{end\ seating\ position}$ on the ZX plane about the point Q by one half the forward tilt angle H7 of the trunk. Similarly, $Z_{forward\ bending\ intermediate\ point}$ can be determined by rotating $Z_{end\ seating\ position}$ on the ZX plane about the point Q by one half the forward tilt angle H7 of the trunk.

In such a manner, the forward bending line calculation unit 14 separately calculates the foregoing forward bending intermediate point for the case where the patient takes the end seating position on the left end of the bed 3 and for the case where the patient takes the end seating position on the right end of the bed 3. The forward bending line calculation unit 14 further calculates the forward bending intermediate points at pitches with which the Y coordinates where the bed 3 exists in the three-dimensional space of the ground coordinate system are sectioned at regular intervals, such as in units of 10 cm, in the depth direction of the bed 3.

The forward bending line calculation unit 14 then connects forward bending intermediate points adjoining in the depth direction of the bed 3, among the foregoing forward bending intermediate points, to calculate forward bending lines for the left and right end seating positions, respectively.

The second parameter acquisition unit 15 is a processing unit that obtains second parameters. Unlike the foregoing first parameters, the "second parameters" as employed herein refer to parameters about the camera 20. Examples include the coordinates where the camera 20 is installed in the three-dimensional space of the ground coordinate system, rotation angles of the camera 20 such as pan, tilt, and roll angles, and resolution and lens distortion of the camera 20.

In one embodiment, the second parameter acquisition unit 15 can obtain the foregoing second parameters by input operations via a not-illustrated input device. The second parameter acquisition unit 15 can also obtain the second parameters from an auxiliary storage device such as a hard disk and an optical disk, or a removable medium such as a memory card and a USB memory. The second parameter acquisition unit 15 can further receive and obtain the second parameters from an external apparatus via a network.

The coordinate conversion unit 16 is a processing unit that performs coordinate conversion.

In one embodiment, the coordinate conversion unit 16 converts the coordinates of the head movement paths calculated by the movement path calculation unit 13 and the coordinates of the forward bending lines calculated by the forward bending line calculation unit 14 from the ground coordinate system into the camera coordinate system according to the installation position and the rotation angle of the camera 20 in the ground coordinate system, included in the second parameters obtained by the second parameter acquisition unit 15. The coordinate conversion unit 16 then projects the rotation angle and the coordinates of the head movement paths and the forward bending lines, converted into the camera coordinate system, onto the two-dimensional image coordinate system according to the number of pixels and the lens distortion of the camera 20 included in the second parameters. The coordinate conversion unit 16 thereby converts the coordinates of the head movement paths and the forward bending lines from the camera coordinate system into the image coordinate system.

Here, the coordinate conversion from the ground coordinate system into the image coordinate system is described to be performed via the camera coordinate system. However, the coordinate conversion from the ground coordinate system into the image coordinate system may be performed without the intervention of the camera coordinate system.

Figure 10:
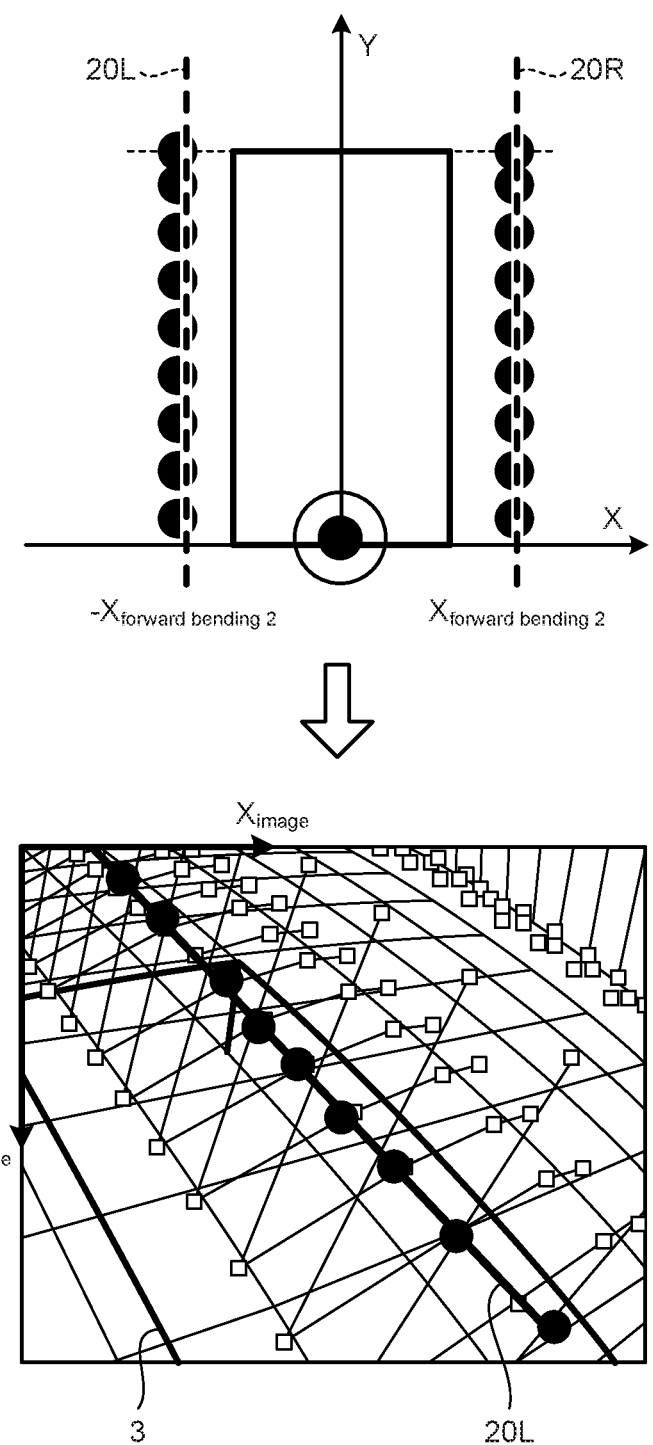
FIG. 10 is a diagram illustrating an example of coordinate conversion.

FIG. 10 is a diagram illustrating an example of the coordinate conversion. The upper part of FIG. 10 illustrates plots of the forward bending intermediate points on the XY plane of the ground coordinate system, along with forward bending lines 20L and 20R. The forward bending lines 20L and 20R are formed by connecting the forward bending intermediate points of the left and right end seating positions, respectively, on the XY plane of the ground coordinate system. The forward bending lines 20L and 20R are converted from the ground coordinate system into the image coordinate system as illustrated in the lower part of FIG. 10. The lower part of FIG. 10 illustrates a case where the camera 20 captures the bed 3 from the head side of the bed 3, obliquely from the left. Between the forward bending lines 20L and 20R, the forward bending line 20L is illustrated. The forward bending line 20R is similarly converted into the image coordinate system. As illustrated in the lower part of FIG. 10, the forward bending lines 20L and 20R are converted from the three-dimensional ground coordinate system into the two-dimensional image coordinate system with the upper left corner of the image as the origin.

The setting unit 17 is a processing unit that makes various settings about the behavior detection apparatus 100.

Figure 11:
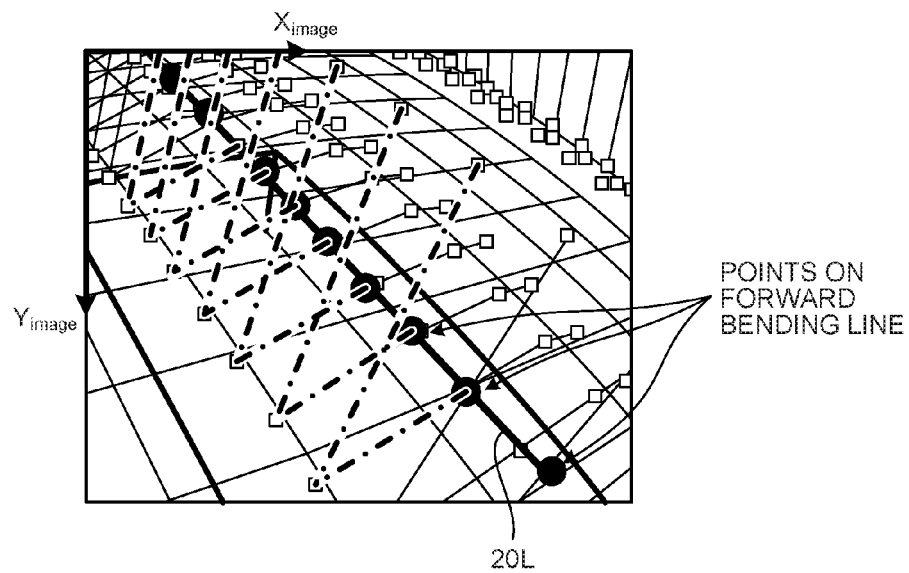
FIG. 11 is a diagram illustrating an example of predicted lines of head movement paths.

In one embodiment, the setting unit 17 sets the forward bending lines 20L and 20R converted into the image coordinate system by the coordinate conversion unit 16, as reference data into a work area of an internal memory which a first passing determination unit 120 of the behavior detection apparatus 100 refers to. The setting unit 17 further determines intersections between the forward bending lines 20L and 20R and the head movement paths in the image coordinate system. With respect to each of the intersections where the forward bending lines 20L and 20R and the head movement paths intersect, the setting unit 17 then extracts a partial movement path of the head movement path past the intersection up to the standing position as a predicted line of the head movement path. The setting unit 17 then sets the predicted line of the head movement path with respect to each intersection into a work area of the internal memory which a stand-up line setting unit 130 of the behavior detection apparatus 100 refers to. FIG. 11 is a diagram illustrating an example of the predicted lines of the head movement paths. FIG. 11 illustrates the forward bending line 20L illustrated in the lower part of FIG. 10, excerpted from the forward bending lines 20L and 20R. As illustrated in FIG. 11, data in which the coordinates of the intersections where the forward bending line 20L and the head path movement paths intersect are associated with the predicted lines of the respective head movement paths, i.e., the dashed dotted lines in the diagram is set for the stand-up line setting unit 130.

The learning unit 18 is a processing unit that performs machine learning.

Figure 12:
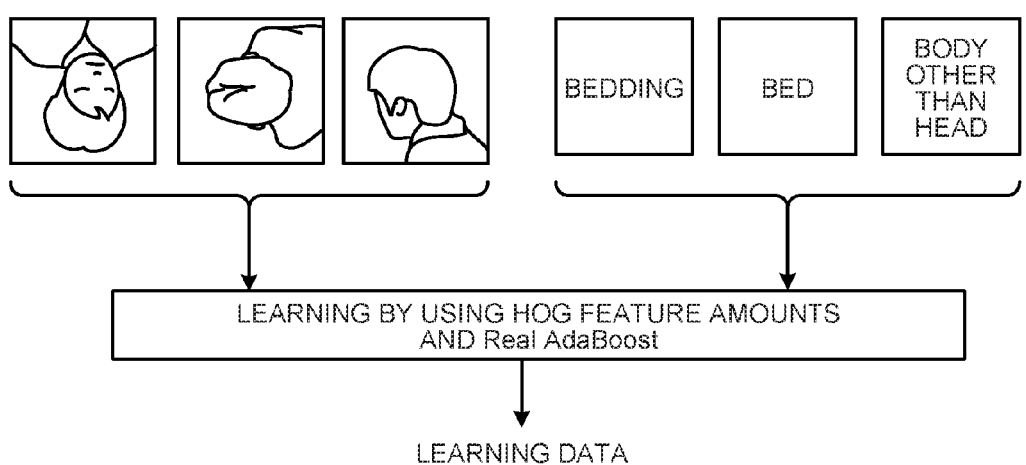
FIG. 12 is a diagram illustrating an example of a learning method.

In one embodiment, the learning unit 18 performs machine learning by using a HOG Real AdaBoost learning model. FIG. 12 is a diagram illustrating an example of the learning method. As illustrated in FIG. 12, the learning unit 18 learns HOG feature amounts of learning samples according to a Real AdaBoost algorithm. The learning samples include positive data on human heads, and negative data on bedding, beds, and bodies other than heads. The learning unit 18 thereby generates a Real AdaBoost classifier as an identifier for head detection. The identifier for head detection generated thus is set as a determination model which a head detection unit 110 of the behavior detection apparatus 100 uses.

The foregoing processing units including the first parameter acquisition unit 11, the model generation unit 12, the movement path calculation unit 13, the forward bending line calculation unit 14, the second parameter acquisition unit 15, the coordinate conversion unit 16, the setting unit 17, and the learning unit 18 can be implemented in the following manner. For example, the foregoing processing units can be implemented by a central processing unit (CPU) loading processes for exerting the same functions as those of the foregoing processing units into a memory and executing the processes. Such functional units need not necessarily be executed by the central processing unit, and may be executed by a micro processing unit (MPU). The foregoing functional units may be implemented as hardwired logic such as an application specific integrated circuit (ASIC) and a field programmable gate array (FPGA).

For example, various semiconductor memory devices such as a random access memory (RAM) and a flash memory may be employed as a main storage device used by the foregoing processing units. The storage device for the foregoing processing units to refer to need not necessarily be a main storage device, and may be an auxiliary storage device. In such a case, a hard disk drive (HDD), an optical disk, a solid state drive (SSD), and the like may be employed.

Configuration of Behavior Detection Apparatus 100

Next, a functional configuration of the behavior detection apparatus 100 according to the present embodiment will be described. As illustrated in FIG. 1, the behavior detection apparatus 100 includes the head detection unit 110, the first passing determination unit 120, the stand-up line setting unit 130, a second passing determination unit 140, and a notification unit 150.

The head detection unit 110 is a processing unit that detects a head from an image.

Figure 13:
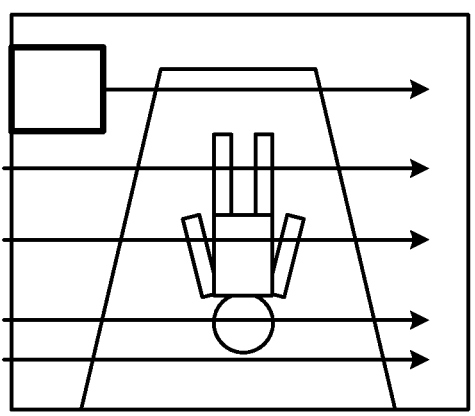
FIG. 13 is a diagram illustrating an example of a scanning method.

In one embodiment, the head detection unit 110 activates processing each time an image is captured by the camera 20. FIG. 13 is a diagram illustrating an example of a scanning method. As illustrated in FIG. 13, the head detection unit 110 performs raster scan on the image captured by the camera 20. The head detection unit 110 thereby detects a position, e.g., barycentric position of a head by using the identifier for head detection generated by the learning unit 18.

The first passing determination unit 120 is a processing unit that determines whether the head passes a forward bending line.

In one embodiment, the first passing determination unit 120 determines whether a track that connects the positions of the head detected by the head detection unit 110 between the frame of the image captured by the camera 20 and a frame captured before the frame, e.g., the previous frame passes either one of the forward bending lines 20L and 20R set by the setting unit 17. By determining the passing of the forward bending lines 20L and 20R, the first passing determination unit 120 can determine that any one of motions including forward bending as a preliminary motion of standing up, a roll-over, and a motion in a sitting position such as a motion of picking up an object placed on the ground is being made. At the stage of first passing of the forward bending line 20L or 20R, the preliminary motion of standing up and the other motions are not distinguished. Such a distinction is left to the second passing determination unit 140.

The stand-up line setting unit 130 is a processing unit that sets a stand-up line on the image.

In one embodiment, if the first passing determination unit 120 determines that the patient's head passes the forward bending line 20L or 20R, the stand-up line setting unit 130 determines the coordinates of the passing point where the track of the position of the head detected by the head detection unit 110 passes the forward bending line 20L and 20R. The stand-up line setting unit 130 then obtains a predicted line that is associated with an intersection P at a shortest distance from the passing point of which the coordinates are determined, among the predicted lines of the head movement paths stored in the internal memory.

Figure 14:
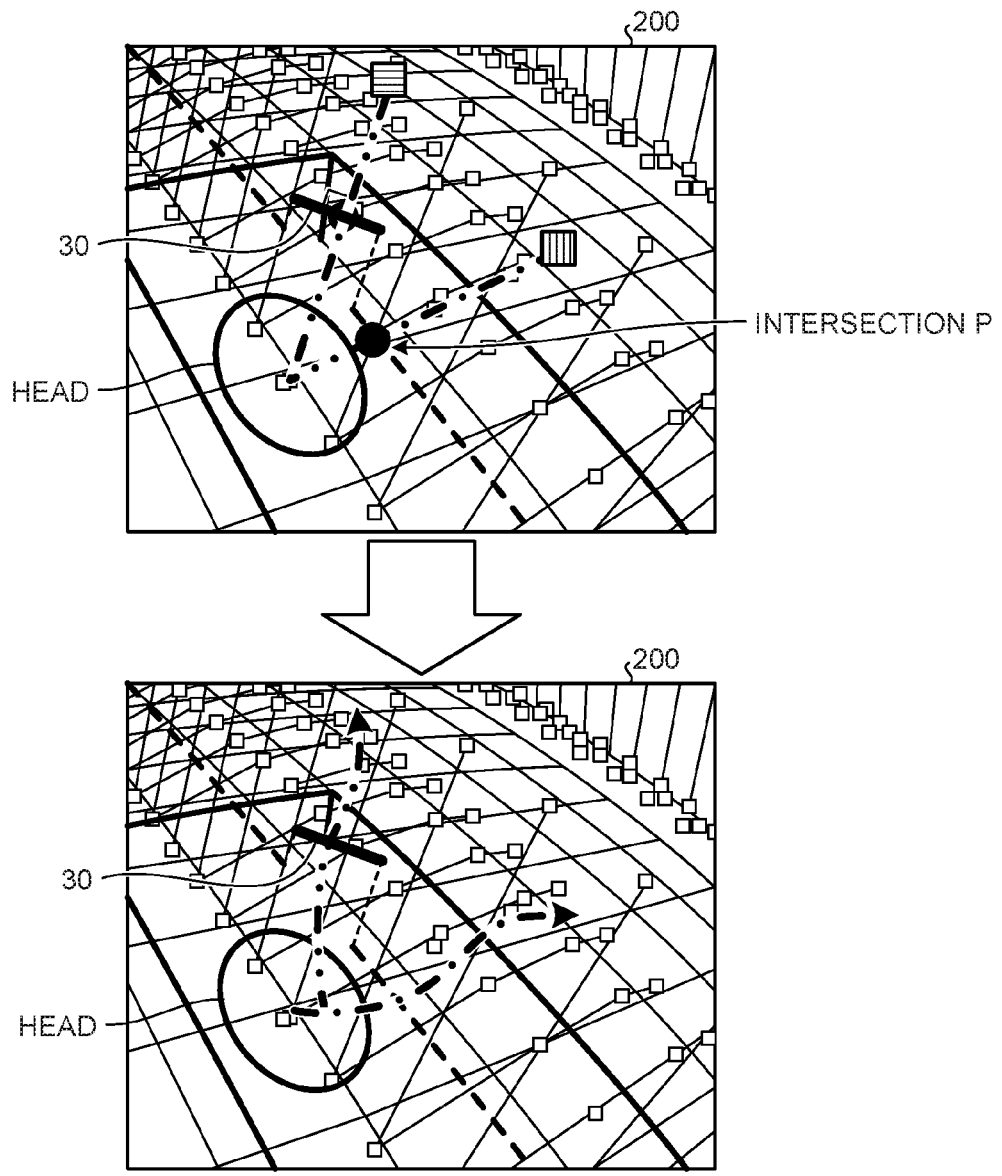
FIG. 14 is a diagram illustrating an example of a method for setting a stand-up line.

FIG. 14 is a diagram illustrating an example of the method for setting a stand-up line. The reference numeral 200 illustrated in FIG. 14 designates an image captured by the camera 20. The upper part of FIG. 14 illustrates the head movement path corresponding to the intersection P corresponding to the passing point. Specifically, in the upper part of FIG. 14, a rectangle filled with vertical lines indicates the position of the head in an end seating position. A rectangle filled with horizontal lines indicates the predicted position of the head in a standing position by the bed 3. Moreover, in the upper part of FIG. 14, a dashed dotted line represents the path in which the patient's head has moved to the intersection P. A dashed double-dotted line represents the path in which the patient's head past the intersection P is predicted to move to the standing position, i.e., the predicted line of the mead movement path.

If the predicted line of the head movement path illustrated in the upper part of FIG. 14 is obtained, the stand-up line setting unit 130 sets a stand-up line 30 described above, which is the thick solid line illustrated in FIG. 14. The stand-up line 30 is set in a normal direction with respect to a line segment of the predicted line of the head movement path, the line segment connecting the position of the head in the forward bending position, i.e., the lowest point and the position of the head in the standing position, i.e., the position of the head in the standing position by the bed 3. Such a stand-up line 30 may be set in an arbitrary position on the foregoing line segment. In the example illustrated in the upper part of FIG. 14, the stand-up line 30 is set at the position of the midpoint of the line segment. The stand-up line 30 set in such a manner allows a distinction as to whether the subsequent behavior is a stand-up motion or other motions.

In the lower part of FIG. 14, a dashed dotted line represents an actual example of the head movement path when the patient does not stand up after the forward bending posture, like when the patient picks up an object on the ground. A dashed double-dotted line represents an actual example of the head movement path when the patient stands up after the forward bending posture. As illustrated in the lower part of FIG. 14, if the patient stands up after the forward bending posture, as represented by the dashed double-dotted line in the lower part of FIG. 14, the patient's head traces a tilted L-shaped path before and after the forward bending posture. It can also be seen that if the patient does not stand up after the forward bending posture, the patient's head is likely to return, after the forward bending posture, to the vicinity of the head position prior to the forward bending of the patient. According to the foregoing stand-up line 30, the stand-up line 30 can be set in a position where the patient's head passes only if the head moves along the L-shaped path after the forward bending posture.

If the stand-up line 30 is set thus, the stand-up line setting unit 130 deletes a part of the forward bending line, or more specifically, a predetermined range with respect to the portion where the predicted line of the head movement path passes. The purpose is to allow either one of the events including the passing of the stand-up line 30 and second passing of the forward bending line 20 to occur selectively. In other words, the purpose is to, if the forward bending line 20 is determined to be passed for the second time, determine that a motion other than standing up is made, and cancel the stand-up line 30.

The second passing determination unit 140 is a processing unit that determines which line the head passes, the stand-up line or the forward bending line.

In one embodiment, the second passing determination unit 140 is run each time the position of the head is detected from the image by the head detection unit 110 after the stand-up line 30 is set by the stand-up line setting unit 130 until the stand-up line 30 is cancelled. In other words, the second passing determination unit 140 determines whether the track connecting the positions of the head detected by the head detection unit 110 between the frame of the image captured by the camera 20 and the previous frame passes the stand-up line 30.

If the track passes the stand-up line 30, the patient is likely to stand up with the forward bending as a preliminary motion. In such a case, the notification unit 150 makes a notification to a person or persons concerned. On the other hand, if the track does not pass the stand-up line 30, the second passing determination unit 140 determines whether the track connecting the positions of the head between the frames of the image passes the forward bending line 20. If the track passes the forward bending line, the patient is likely to have taken the forward bending posture for purposes other than standing up. In such a case, the notification unit 150 makes no notification to the person(s) concerned. Then, the stand-up line 30 is canceled by the stand-up line setting unit 130, and the deletion of the part of the forward bending line is cancelled.

The notification unit 150 is a processing unit that performs various types of notification.

In one embodiment, if the second passing determination unit 140 determines that the stand-up line 30 is passed, the notification unit 150 can output a notification to arbitrary output destinations, including a not-illustrated display device and voice output device included in the behavior detection apparatus 100. For example, the output destinations may include terminal devices used by people concerned with the user of the bed 3, such as the patient's family members, nurses, doctors, and caregivers in charge of care of the person in need of nursing care. Notification sound for notifying of the bed leaving, such as electronic sound and a message, may be output from a speaker and the like in the facility's control room or nurses' station.

The foregoing processing units including the head detection unit 110, the first passing determination unit 120, the stand-up line setting unit 130, the second passing determination unit 140, and the notification unit 150 can be implemented in the following manner. For example, the processing units may be implemented by a central processing unit (CPU) loading processes for exerting the same functions as those of the foregoing processing units into a memory and executing the processes. Such functional units need not necessarily be executed by the central processing unit, and may be executed by an MPU. The foregoing functional units may be implemented as hardwired logic such as an ASIC and an FPGA.

For example, various semiconductor memory devices such as a RAM and a flash memory may be employed as a main storage device used by the foregoing processing units. The storage device for the foregoing processing units to refer to need not necessarily be a main storage device, and may be an auxiliary storage device. In such a case, an HDD, an optical disk, an SSD, and the like may be employed.

Processing Flow

Next, a flow of processing of the behavior detection system according to the present embodiment will be described. Here, (1) setting processing performed by the setting apparatus 10 will be described before a description of (2) behavior detection processing performed by the behavior detection apparatus 100.

(1) Setting Processing

Figure 15:
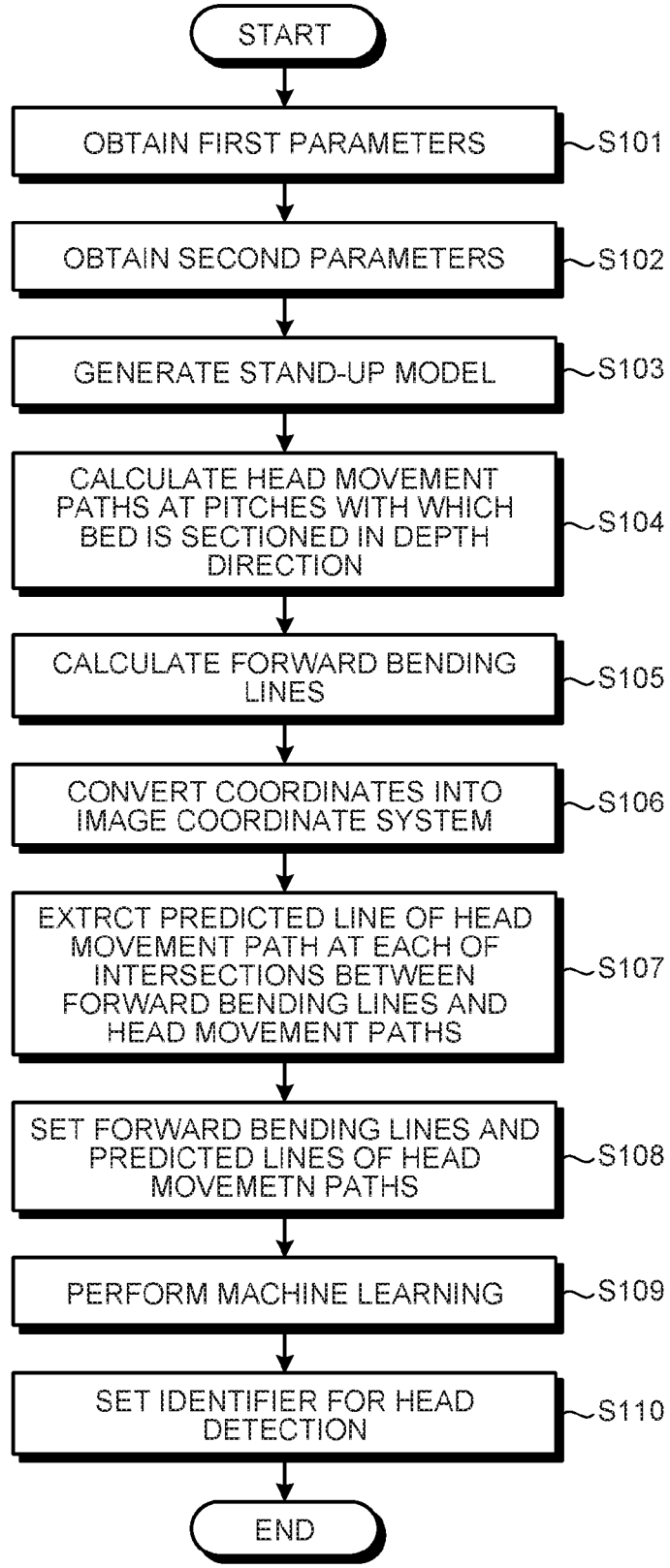
FIG. 15 is a flowchart illustrating a procedure of setting processing according to the first embodiment.

FIG. 15 is a flowchart illustrating a procedure of the setting processing according to the first embodiment. This processing is activated when a setting start instruction is accepted or when the first parameters or second parameters are obtained.

As illustrated in FIG. 15, if the first parameter acquisition unit 11 obtains the first parameters and the second parameter acquisition unit 15 obtains the second parameters (steps S101 and S102), the model generation unit 12 generates a stand-up model of the patient from the foregoing first parameters (step S103).

By using the stand-up model obtained in step S103, the movement path calculation unit 13 then calculates head movement paths at pitches with which the Y coordinates where the bed 3 exists in the three-dimensional space of the ground coordinate system are sectioned at predetermined intervals, for example, in units of 10 cm in the depth direction of the bed 3 (step S104). The forward bending line calculation unit 14 calculates forward bending lines by using the stand-up model obtained in step S103 (step S105).

Subsequently, the coordinate conversion unit 16 converts the coordinates of the head movement paths calculated in step S104 and the forward bending lines calculated in step S105 from the camera coordinate system into the image coordinate system (step S106).

Then, at each of the intersections where the forward bending lines 20L and 20R and the head movement paths intersect, the setting unit 17 extracts a partial movement path of the head movement path past the intersection to a standing position as a predicted line of the head movement path (step S107).

The setting unit 17 then sets the forward bending lines 20L and 20R converted into the image coordinate system in step S106 into the behavior detection apparatus 100 as reference data. The setting unit 17 also sets the predicted lines of the head movement paths extracted at the respective intersections in step S107 into the behavior detection apparatus 100 (step S108).

The learning unit 18 performs machine learning about the HOG feature amounts of learning samples according to the Real AdaBoost algorithm, with positive data on human heads and negative data on bedding, beds, and bodies other than heads as the learning samples (step S109).

The learning unit 18 then sets the Real AdaBoost classifier obtained by the machine learning of step S109 into the behavior detection apparatus 100 as an identifier for head detection (step S110), and ends the processing.

(2) Behavior Detection Processing

Figure 16:
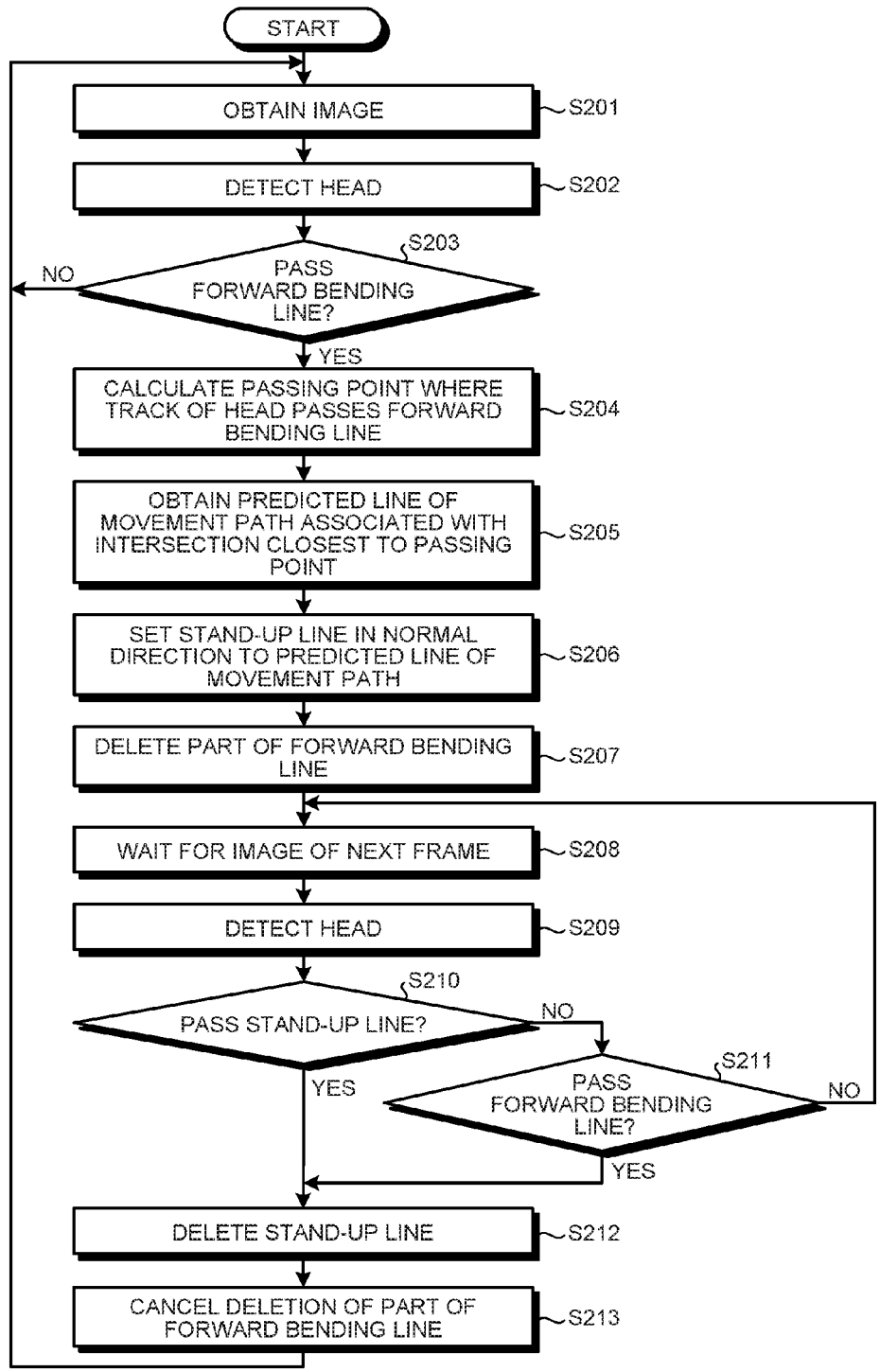
FIG. 16 is a flowchart illustrating a procedure of behavior detection processing according to the first embodiment.

FIG. 16 is a flowchart illustrating a procedure of the behavior detection processing according to the first embodiment. This processing is repeated as long as there is an output of an image from the camera 20. As illustrated in FIG. 16, if an image is obtained from the camera 20 (step S201), the head detection unit 110 detects a position of a head by performing raster scan on the image obtained in step S201, using the identifier for head detection generated by the learning unit 18 (step S202).

The first passing determination unit 120 then determines whether a track connecting the positions of the head between the frame obtained in step S201 and the previous frame passes either one of the forward bending lines 20L and 20R (step S203).

If the first passing determination unit 120 determines that the patient's head passes the forward bending line 20L or 20R (Yes in step S203), the stand-up line setting unit 130 determines the coordinates of the passing point where the track of the position of the head detected by the head detection unit 110 passes the forward bending line 20 (step S204).

The stand-up line setting unit 130 then obtains a predicted line that is associated with an intersection P at a shortest distance from the passing point determined in step S204 among the predicted lines of the head movement paths stored in the internal memory (step S205).

The stand-up line setting unit 130 then sets a stand-up line in a normal direction with respect to a line segment of the predicted line of the head movement path, the line segment connecting the lowest point of the forward bending and the position of the head in the standing position. The stand-up line setting unit 130 further deletes a part of the forward bending line, or more specifically, a predetermined range with respect to the portion where the predicted line of the head movement path passes (steps S206 and S207).

Subsequently, the second passing determination unit 140 waits until an image of the next frame is obtained (step S208). The head detection unit 110 detects the position of the head from the image of the frame obtained in step S208 (step S209).

The second passing determination unit 140 then determines whether a track connecting the positions of the head between the frame obtained in step S208 and the previous frame passes the stand-up line 30 (step S210).

If the track passes the stand-up line 30 (Yes in step S210), the patient is likely to stand up with the forward bending as a preliminary motion. In such a case, the notification unit 150 makes a notification to the person(s) concerned. On the other hand, if the track does not pass the stand-up line 30 (No in step S210), the second passing determination unit 140 further determines whether the track connecting the positions of the head between the frames of the image passes the forward bending line 20 (step S211). If the track passes the forward bending line (Yes in step S211), the patient is likely to have taken the forward bending posture for purposes other than standing up. In such a case, the notification unit 150 makes no notification to the person(s) concerned. If No in step S210 and No in step S211, the second passing determination unit 140 returns to step S208 to repeat the subsequent processing.

If Yes in the foregoing step S210 or Yes in step S211, the stand-up line setting unit 130 cancels the stand-up line 30 set in step S206 and cancels the deletion of the part of the forward bending line (steps S212 and S213), and returns to the processing of step S201.

One Aspect of Effect

As has been described above, the behavior detection system 1 according to the present embodiment dynamically sets a line for determining bed leaving according to the movement path of a head predicted in the case of standing up from a forward bending posture detected from an image captured by the camera 20, and determines whether the head passes the line. As a result, even if the line used for the foregoing determination of the bed leaving is set in an area where the bed appears in the image captured by the camera 20, the occurrence of false detection of the bed leaving due to motions made on the bed other than standing up, such as a roll-over and a motion in a sitting position, can be suppressed. Consequently, according to the behavior detection system 1 according to the present embodiment, the flexibility of the installation position of the camera 20 used for the detection of the bed leaving can be increased.

[b] Second Embodiment

One embodiment related to the disclosed apparatuses has been described above. However, the present invention may be practiced in various other forms than the foregoing embodiment. Other embodiments included in the present invention will be described below.

Setting of Wake-Up Line

In the foregoing the first embodiment, the behavior detection processing is described to be performed with the forward bending lines always activated on the image. However, the forward bending lines need not necessarily be always set to an ON state. Then, a case will be described below in which a wake-up line for determining whether the patient is in a recumbent position or in a sitting position on the bed 3 is set, and the forward bending lines are deactivated if the head is inside the wake-up line.

Figure 17:
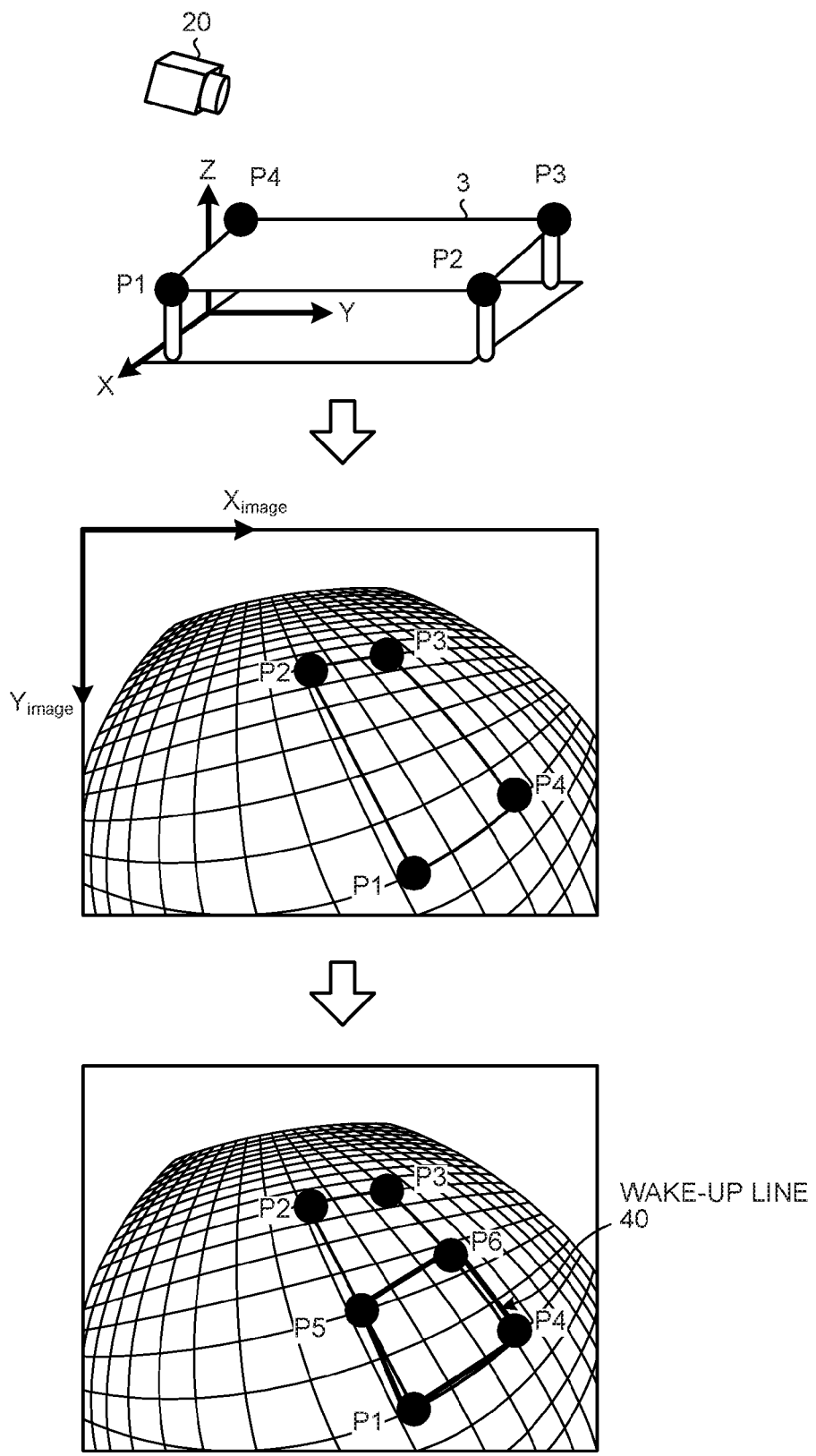
FIG. 17 is a diagram illustrating an example of a method for setting a wake-up line.

FIG. 17 is a diagram illustrating an example of a method for setting wake-up lines. The top part of FIG. 17 illustrates four vertexes P1 to P4 included by the bed surface of the bed 3 in the ground coordinate system. As illustrated in the middle part of FIG. 17, the setting apparatus 10 converts the three-dimensional coordinates of the four vertexes P1 to P4 into two-dimensional coordinates of the image coordinate system. As illustrated in the bottom part of FIG. 17, the setting apparatus 10 then extracts a midpoint P5 between the vertexes P1 and P2 and a midpoint P6 between the vertexes P3 and P4. The setting apparatus 10 then sets an area formed by four points including the vertex P1, the midpoint P5, the midpoint P6, and the vertex P4 as a wake-up line 40 into the behavior detection apparatus 100.

Figure 18:
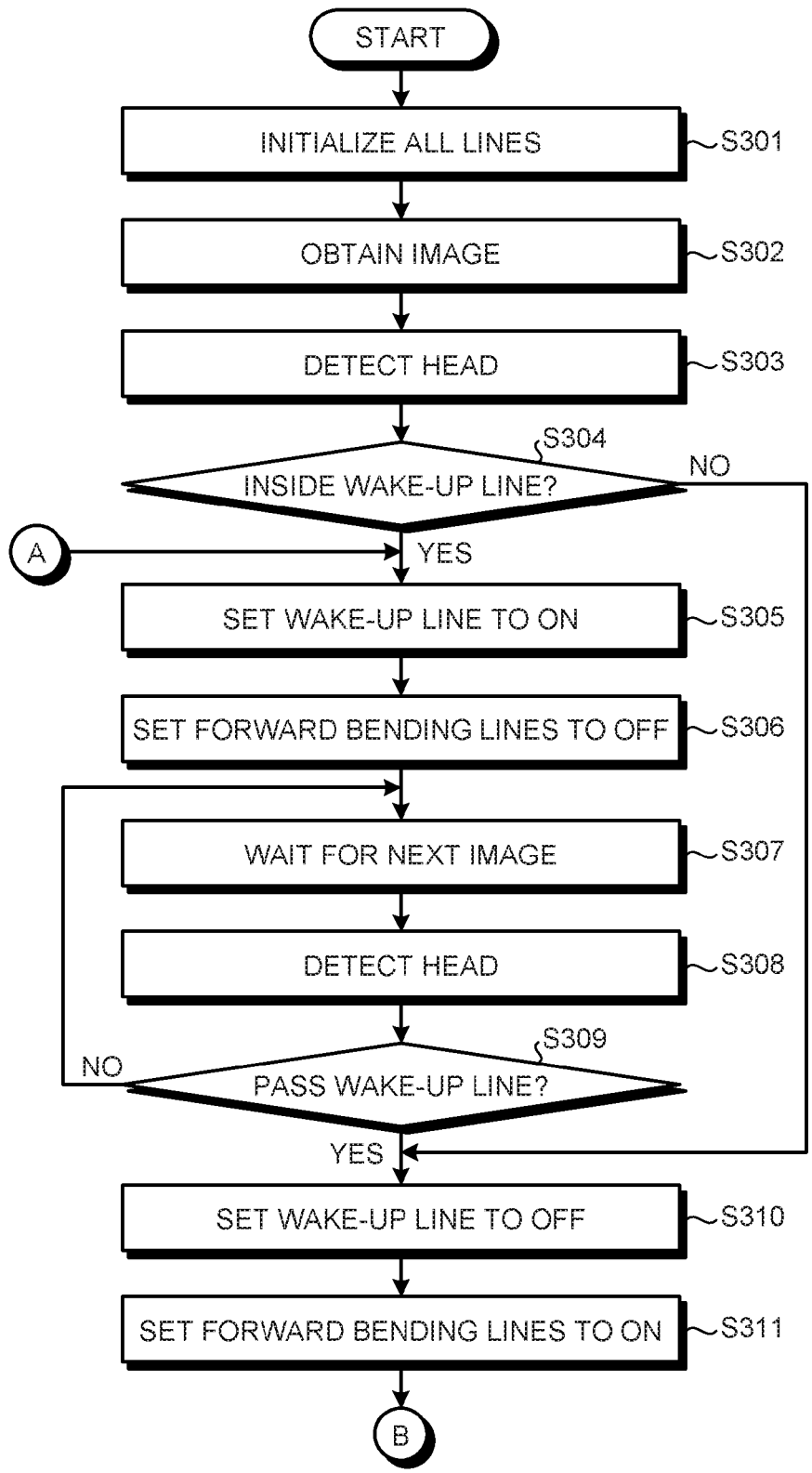
FIG. 18 is a flowchart (1) illustrating a procedure of behavior detection processing according to an application example.
Figure 19:
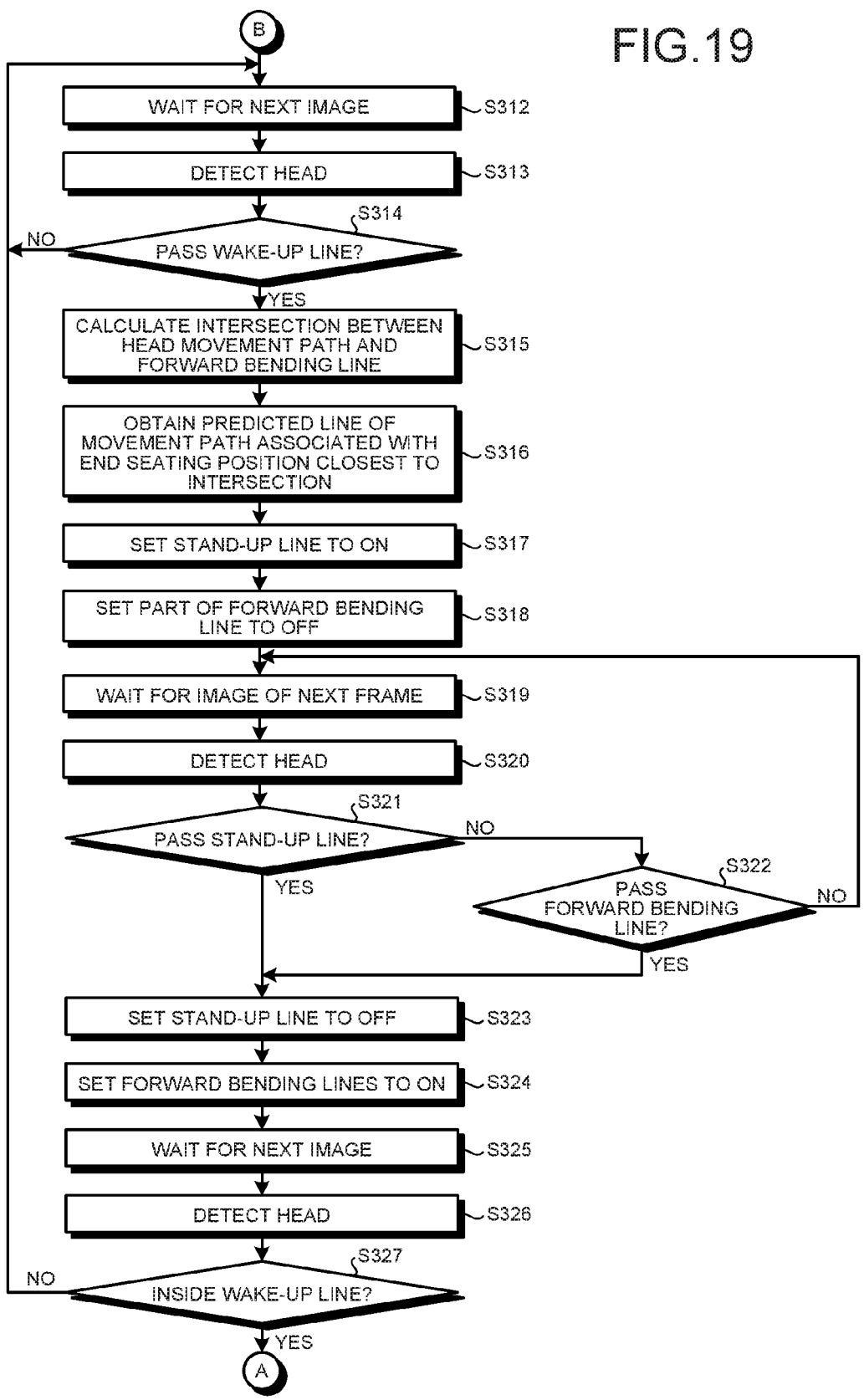
FIG. 19 is a flowchart (2) illustrating the procedure of the behavior detection processing according to the application example.

FIGS. 18 and 19 are flowcharts illustrating a procedure of behavior detection processing according to an application example. As illustrated in FIG. 18, if the behavior detection processing is activated, the behavior detection apparatus 100 initializes all lines by setting the forward bending lines 20, the stand-up line 30, and the wake-up line 40 to an OFF state (step S301).

If an image is obtained from the camera 20 (step S302), the behavior detection apparatus 100 detects the position of a head by performing raster scan on the image obtained in step S302, using the identifier for head detection generated by the learning unit 18 (step S303).

The behavior detection apparatus 100 then determines whether the position of the head detected in step S303 is inside the wake-up line 40 (step S304). If the position of the head is inside the wake-up line 40 (Yes in step S304), the patient is likely to be in a recumbent position. This illustrates that the forward bending lines 20 need not necessarily be set. The reason is that changing the posture from a recumbent position to forward bending is an unnatural motion of going off human's physiological curves. In such a case, the behavior detection apparatus 100 sets the wake-up line 40 to an ON state and sets the forward bending lines 20 to an OFF state (steps S305 and S306). As a result, the wake-up motion of changing the posture from a recumbent position to a sitting position is monitored. If the position of the head is outside the wake-up line 40 (No in step S304), the behavior detection apparatus 100 proceeds to step S310 to be described later.

The behavior detection apparatus 100 then waits until an image of the next frame is obtained (step S307), and detects the position of the head from the image of the frame obtained in step S307 (step S308). The behavior detection apparatus 100 repeats the processing of the foregoing steps S307 and S308 until the position of the head detected from the image of the frame obtained in step S307 passes the wake-up line 40 (while No in step S309).

If the position of the head detected from the image of the frame obtained in step S307 passes the wake-up line 40 (Yes in step S309), the patient is estimated to be likely to have risen from a recumbent position to a sitting posture. In such a case, the behavior detection apparatus 100 sets the wake-up line 40 to an OFF state and sets the forward bending lines 20 to an ON state (steps S310 and S311).

The behavior detection apparatus 100 then waits until an image of the next frame is obtained (step S312), and detects the position of the head from the image of the frame obtained in step S312 (step S313).

Next, the behavior detection apparatus 100 determines whether a track connecting the positions of the head between the frame obtained in step S312 and the previous frame passes either one of the forward bending lines 20L and 20R (step S314).

If the patient's head passes the forward bending line 20L or 20R (Yes in step S314), the behavior detection apparatus 100 determines the passing point between the track of the position of the head and the forward bending line 20 of which the passing is detected (step S315).

Next, the behavior detection apparatus 100 obtains a predicted line that is associated with an intersection P at a shortest distance from the passing point determined in step S315 among the predicted lines of the head movement paths stored in the internal memory (step S316).

The behavior detection apparatus 100 then sets a stand-up line 30 in a normal direction with respect to a line segment of the predicted line of the head movement path, the line segment connecting the lowest point of the forward bending and the position of the head in the standing position, and sets the stand-up line 30 to an ON state. The behavior detection apparatus 100 also deletes a part of the forward bending line 20, or more specifically, a predetermined range with respect to the portion where the predicted line of the head movement path passes (steps S317 and S318).

The behavior detection apparatus 100 then waits until an image of the next frame is obtained (step S319), and detects the position of the head from the image of the frame obtained in step S319 (step S320).

The behavior detection apparatus 100 then determines whether a track connecting the positions of the head between the frame obtained in step S319 and the previous frame passes the stand-up line 30 (step S321).

If the track passes the stand-up line 30 (Yes in step S321), the patient is likely to stand up with the forward bending as a preliminary motion. In such a case, the notification unit 150 makes a notification to the person(s) concerned. On the other hand, if the track does not pass the stand-up line 30 (No in step S321), the behavior detection apparatus 100 further determines whether the track connecting the positions of the head between the frames of the image passes the forward bending line 20 (step S322). If the track passes the forward bending line (Yes in step S322), the patient is likely to have taken the forward bending posture for purposes other than standing up. In such a case, the notification unit 150 makes no notification to the person(s) concerned. If No in step S321 and No in step S322, the behavior detection apparatus 100 returns to step 319 to repeat the subsequent processing.

If Yes in the foregoing step S321 or Yes in step S322, the behavior detection apparatus 100 sets the stand-up line 30 set to the ON state in step S317 to an OFF state. The behavior detection apparatus 100 also cancels the deletion of the part of the forward bending line 20 and sets the entire forward bending line 20 to an ON state (steps S323 and S324).

The behavior detection apparatus 100 then waits until an image of the next frame is obtained (step S325), and detects the position of the head from the image of the frame obtained in step S325 (step S326).

Here, if the position of the head is inside the wake-up line 40 (Yes in step S327), the behavior detection apparatus 100 proceeds to step S305 and continues processing. On the other hand, if the position of the head is not inside the wake-up line 40 (No in step S327), the behavior detection apparatus 100 proceeds to step S312 and continues processing.

By the foregoing setting of the wake-up line 40, the forward bending lines 20 can be cancelled if the patient is lying in the bed 3. This can suppress the passing of the forward bending lines 20 by the patient's head in the image due to a roll-over and the like. The accuracy of detection of bed leaving is thus expected to improve. The forward bending lines 20 can be set to an ON state on such occasions as when the patient takes a sitting position on the bed 3, after a stand-up is detected, when the patient is absent from the room where the bed 3 is installed, and when the patient is standing by the bed 3. This can suppress the omission of detection of the bed leaving.

Accommodation of Individual Differences

The foregoing the first embodiment has dealt with the case where the stand-up line 30 is set in the normal direction with respect to the predicted line of the head movement path. However, the stand-up line 30 may be set in other directions.

Specifically, the calculation of the stand-up line 30 uses the parameters about the physical sizes and motions of the patient, and is thus susceptible to individual differences. A difference in the speed of the stand-up motion does not affect the determination of the passing of the start-up line 30 and can thus be ignored. Differences in the physical sizes can be accommodated by the input at the time of initialization. In contrast, patient-to-patient individual differences in motion may be difficult to accommodate in advance.

Figure 20:
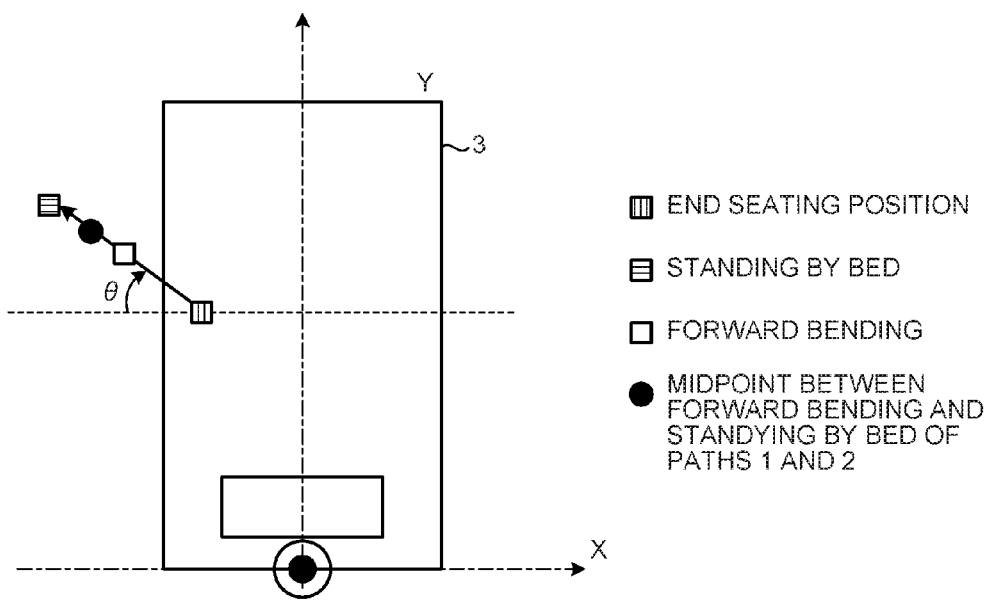
FIG. 20 is a diagram illustrating an example of a stand-up motion.

Then, a stand-up motion can sometimes be performed while the position of the head is deviated from the stand-up line 30 because the patient's motion differs from assumed parameters that are used when constructing the stand-up model. For example, suppose that among the first parameters illustrated in FIG. 6, the parameters H7 and H8 related to the patient's motion are set as (H7, H8)=(40 deg, 200 mm). If H7 and H8 measured in an actual motion are (H7, H8)=(20 deg, 100 mm), the patient can stand up without passing the stand-up line 30. Similar situations can also occur if the patient stands up from the bed 3 obliquely to the width direction of the bed 3. FIG. 20 is a diagram illustrating an example of stand-up motions. As illustrated in FIG. 20, the patient in an end seating position does not necessarily bend forward or make a stand-up motion in the width direction of the bed 3, or in the present example, directly to the left. In some situations, the patient may bend forward or make a stand-up motion in a direction deviated by an angle θ from directly to the left. To accommodate such situations, the stand-up line 30 may be set to be greater in length. Alternatively, a stand-up line 30 may be calculated in the following manner to accommodate the situations.

Figure 21:
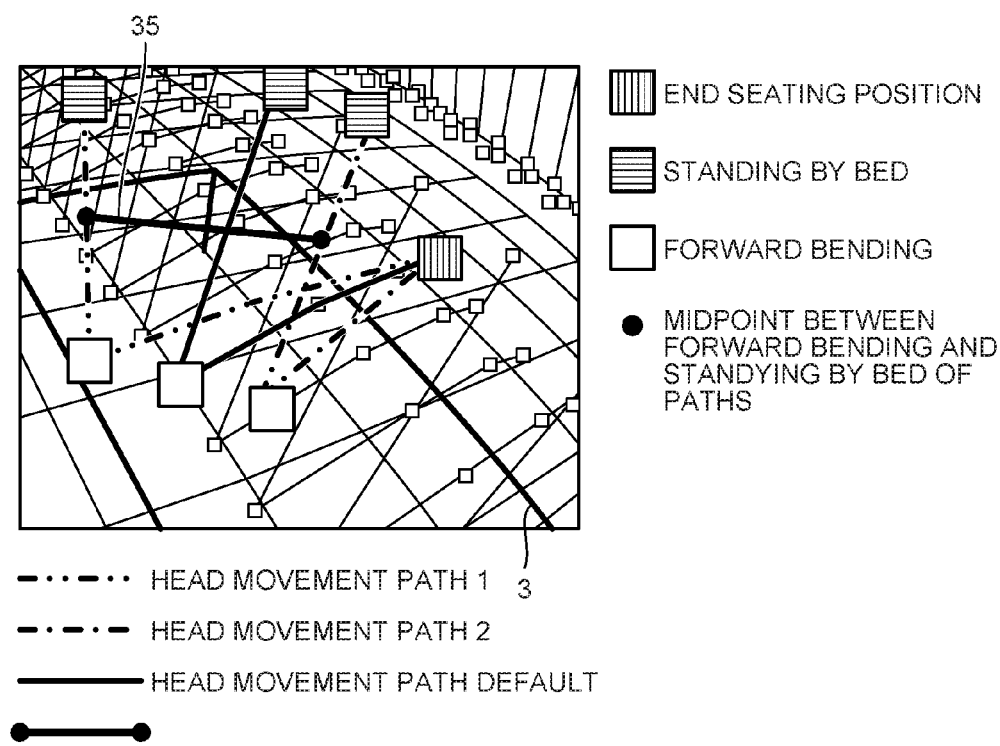
FIG. 21 is a diagram illustrating an application example of the method for setting a stand-up line.

FIG. 21 is a diagram illustrating an application example of the method for setting the stand-up line. FIG. 22 is a diagram illustrating an application example of the setting of parameters related to the motion. A head movement path 1 illustrated by a dashed double-dotted line in FIG. 21 is a path of which the parameters H7, H8, and 8 of the motion illustrated in FIG. 22 are set to be minimum or maximum so that the movement path shifts to a leftmost position in the image coordinate system. In terms of the ground coordinate system, the movement path is shifted farther in the depth direction of the bed 3. A head movement path 2 illustrated by a dashed dotted line in FIG. 22 is a path of which the parameters H7, H8, and 8 of the motion illustrated in FIG. 22 are set to be to be minimum or maximum so that the movement path shifts to a rightmost position in the image coordinate system. In terms of the ground coordinate system, the movement path is shifted nearer in the depth direction of the bed 3. A head movement path default illustrated by a solid line in FIG. 21 is a path calculated from the averages of the parameters of the head movement paths 1 and 2. The head movement path default is the same as the head movement path illustrated in FIG. 14. Then, a line segment that connects the midpoints between the lowest position of the head in a forward bending posture and the position of the head in a standing position by the bed 3 of the respective head movement paths 1 and 2 is set to be a stand-up line 35. As a result, even if there are individual differences in motion, the position of the head passes the stand-up line 35 during a stand-up motion, whereby the omission of detection of the bed leaving can be suppressed. If the predicted line of the head movement path corresponding to an intersection is extracted in step S107 illustrated in FIG. 15, the foregoing head movement paths 1 and 2 may be associated with the intersection between the head movement path (default path) and the forward bending line 20. Then, such a stand-up line 35 can be used in steps S205 and S206 illustrated in FIG. 16.

Fixed Setting of Stand-Up Line

In the foregoing the first embodiment, the stand-up line 30 is described to be dynamically set on condition that the head passes a forward bending line on the image. However, the stand-up line 30 need not necessarily be set dynamically. For example, a stand-up line 30 may be fixedly set in the behavior detection apparatus 100. If the head passes the stand-up line, bed leaving can be detected depending on whether the head has passed a forward bending line within a predetermined number of frames in the past.

For example, using the foregoing stand-up model, the behavior detection apparatus 100 determines the position of the head in an arbitrary intermediate position on the movement path through which the patient's head moves from the lowest point of the forward bending to the standing position. Here, as an example, a case of determining the position of the head at the midpoint of the movement path through which the patient's head moves from the lowest point of the forward bending to the standing position will be described. In the following description, the midpoint of the movement path through which the patient's head moves from the forward bending to the standing position may be referred to as a "stand-up intermediate point." FIG. 23 is a diagram illustrating an example of the stand-up intermediate point. In FIG. 23, the model of the patient in the forward bending is illustrated by broken lines. The model of the patient in the standing position is illustrated by solid lines. As illustrated in FIG. 23, the position of the head at the stand-up intermediate point is that of the black circle in the diagram. $X_{stand\text{-}up\ intermediate\ point}$ can be determined by using the positions of the head $X_{forward\ bending}$ and $X_{standing\ position\ by\ bed}$. More specifically, the behavior detection apparatus 100 calculates the position $X_{stand\text{-}up\ intermediate\ point}$ of the head in an end seating position by calculating "$(X_{forward\ bending}+X_{standing\ position\ by\ bed})/2$." $Z_{stand\text{-}up\ intermediate\ point}$ can be determined by using the positions of the head $Z_{forward\ bending}$ and $Z_{standing\ position\ by\ bed}$. More specifically, the behavior detection apparatus 100 calculates the position $Z_{stand\text{-}up\ intermediate\ point}$ of the head in the end seating position by calculating "$(Z_{forward\ bending}+Z_{standing\ position\ by\ bed})/2$." For the position $Y_{stand\text{-}up\ intermediate\ point}$ of the head in the end seating position, an arbitrary Y coordinate may be employed as long as the Y coordinate can be projected onto the bed surface of the bed 3 by projection in the Z-axis direction.

Figure 24:
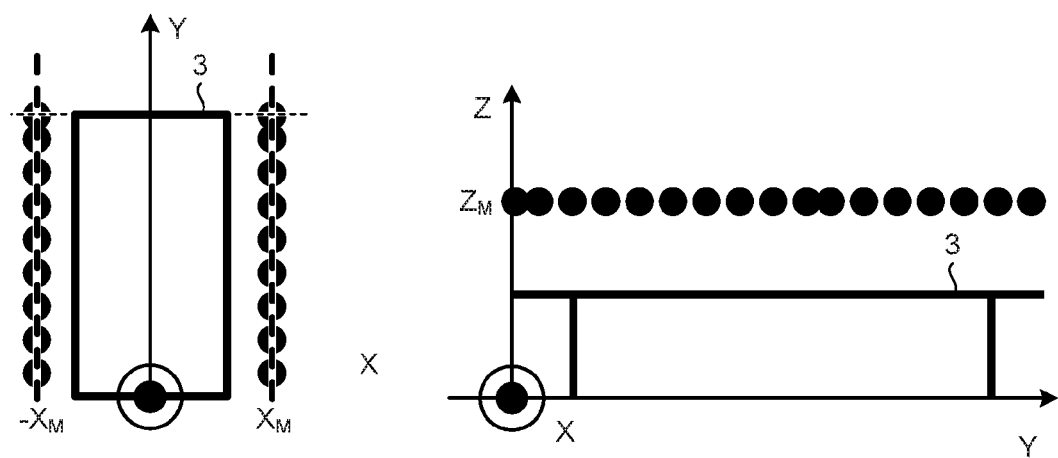
FIG. 24 is a diagram illustrating an example of a calculation result of stand-up intermediate points.

In such a manner, the behavior detection apparatus 100 separately calculates the foregoing stand-up intermediate points for the case where the patient takes an end seating posture on the left end of the bed 3 and for the case where the patient takes an end sating position on the right end of the bed 3. The behavior detection apparatus 100 calculates such stand-up intermediate points at pitches with which the Y coordinates where the bed 3 exists in the three-dimensional space of the ground coordinate system are sectioned at predetermined intervals, such as in units of 10 cm, in the depth direction of the bed 3. The stand-up intermediate points thus calculated are illustrated in FIG. 24. FIG. 24 is a diagram illustrating an example of the calculations of the stand-up intermediate points. In FIG. 24, the stand-up intermediate points are illustrated as plotted on the XY plane and the YZ plane of the ground coordinate system. The behavior detection apparatus 100 then converts the coordinates of the respective stand-up intermediate points from the ground coordinate system into the image coordinate system. The result is illustrated in FIG. 25. FIG. 25 is a diagram illustrating an example of the method for setting a stand-up line. The upper part of FIG. 25 illustrates the stand-up intermediate points as plotted in the image coordinate system. The behavior detection apparatus 100 then connects adjoining ones of the stand-up intermediate points in the depth direction of the bed 3. As illustrated in the lower part of FIG. 25, the behavior detection apparatus 100 thereby calculates stand-up lines 50L and 50R for left and right end seating positions, respectively.

Distribution and Integration

The components of the illustrated apparatuses need not necessarily be physically configured as illustrated. That is, the specific mode of distribution and integration of the apparatuses is not limited to the illustrated one. All or part of the components may be functionally or physically distributed and/or integrated in arbitrary units according to various loads and usages. For example, the head detection unit 110, the first passing determination unit 120, the stand-up line setting unit 130, the second passing determination unit 140, or the notification unit 150 may be connected as an external apparatus of the behavior detection apparatus 100 via a network. The head detection unit 110, the first passing determination unit 120, the stand-up line setting unit 130, the second passing determination unit 140, and the notification unit 150 may be included in respective different apparatuses, and connected via a network to implement the foregoing functions of the behavior detection apparatus 100 in a cooperative manner.

Behavior Detection Program

The various types of processing described in the foregoing embodiments can be implemented by a computer, such as a personal computer and a work station, executing a program prepared in advance. An example of a computer that executes a behavior detection program having the same functions as those of the foregoing embodiments will be described below with reference to FIG. 26.

Figure 26:
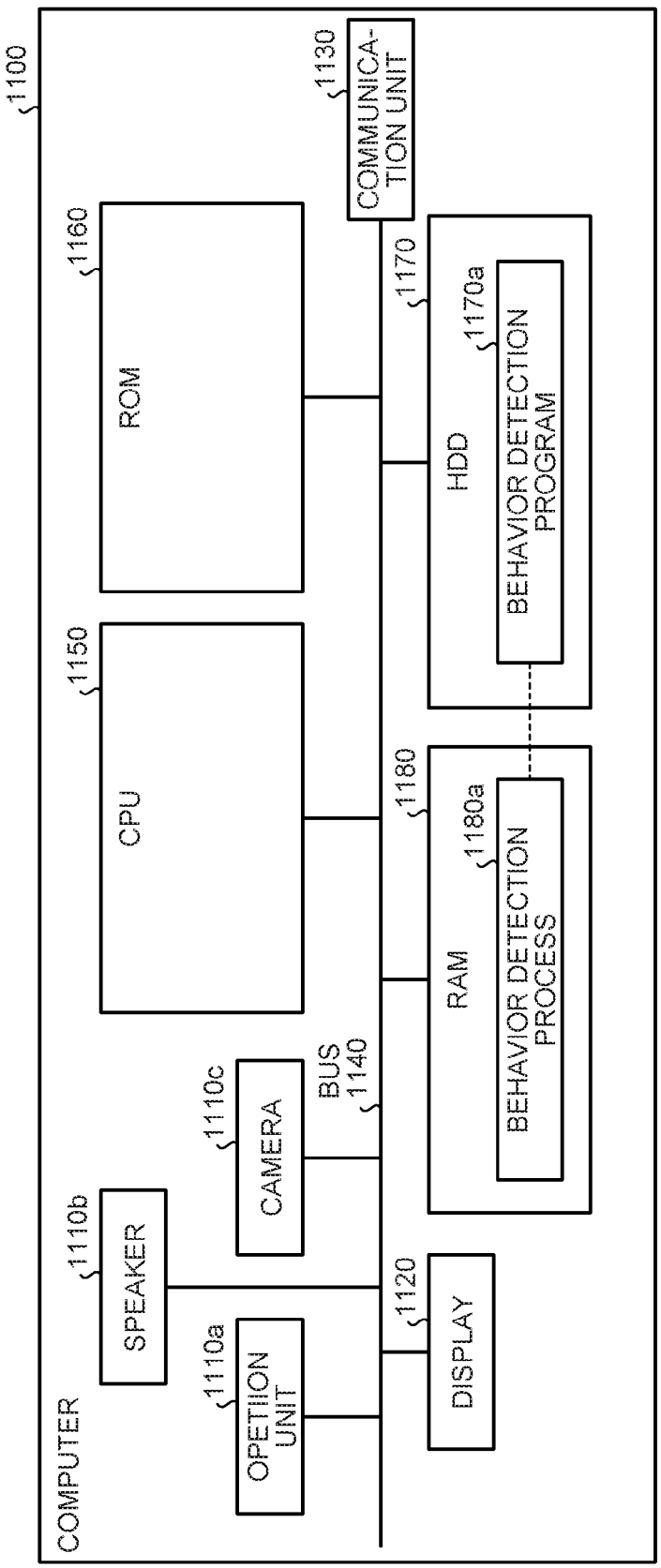
FIG. 26 is a diagram illustrating a hardware configuration example of a computer that executes a behavior detection program according to the first and second embodiments.

FIG. 26 is a diagram illustrating a hardware configuration example of the computer that executes the behavior detection program according to the first and second embodiments. As illustrated in FIG. 26, a computer 1100 includes an operation unit 1110a, a speaker 1110b, a camera 1110c, a display 1120, and a communication unit 1130. The computer 1100 further includes a CPU 1150, a ROM 1160, an HDD 1170, and a RAM 1180. The units 1110 to 1180 are connected via a bus 1140.

As illustrated in FIG. 26, the HDD 1170 stores a behavior detection program 1170a for providing the same functions as those of the head detection unit 110, the first passing determination unit 120, the stand-up line setting unit 130, the second passing determination unit 140, and the notification unit 150. The behavior detection program 1170a may be integrated or separated like the components of the head detection unit 110, the first passing determination unit 120, the stand-up line setting unit 130, the second passing determination unit 140, and the notification unit 150 illustrated in FIG. 1. In other words, the data described in the foregoing the first embodiment need not necessarily be all stored in the HDD 1170. The HDD 1170 has only to store data used for processing.

In such an environment, the CPU 1150 reads the behavior detection program 1170a from the HDD 1170, and loads the behavior detection program 1170a into the RAM 1180. Consequently, as illustrated in FIG. 26, the behavior detection program 1170a functions as a behavior detection process 1180a. The behavior detection process 1180a loads various types of data read from the HDD 1170 into an area allocated for the behavior detection process 1180a in the storage area of the RAM 1180, and performs various types of processing by using the various types of data loaded. Examples of the processing for the behavior detection process 1180a to perform include the processing illustrated in FIG. 16. The CPU 1150 need not necessarily operate all the processing units described in the foregoing the first embodiment. Processing units corresponding to the processing to be executed have only to be virtually implemented.

The foregoing behavior detection program 1170*a* need not necessarily be stored in the HDD 1170 or the ROM 1160 from the beginning. For example, the program may be stored in a "removable physical medium," such as a flexible disk or so-called FD, a CD-ROM, a DVD disk, a magneto-optical disk, and an IC card, to be inserted into the computer 1110. The computer 1100 may then obtain the program from such a removable physical medium and execute the program. The program may be stored in another computer, server apparatus, or the like which is connected to the computer 1100 via a public line, the Internet, a LAN, a WAN, or the like. The computer 1100 may obtain the program from such an apparatus and execute the program.

The flexibility of an installation position of the camera used for the detection of the bed leaving can be increased.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A behavior detection method comprising:
    detecting, by a processor, a position of a head from an image;
    detecting, based on the position of the head, a motion of bending forward when a person to be detected sits up in a width direction of a bed in a bed area of the image and stands up from the sitting state, by the processor;
    when a movement of the head is detected to be forward bending, dynamically setting, based on a movement path of the head, a stand-up detection line for determining bed leaving of the person to be detected between a lowest point of the forward bending and the position of the head when the person to be detected stands by the bed, the stand-up detection line being set in a position not overlapping with a forward bending detection line by which the motion of bending forward is detected, by the processor; and
    detecting, by the processor, a stand-up motion when the head passes the dynamically set stand-up detection line.

2. The behavior detection method according to claim 1, wherein the setting includes setting the stand-up detection line in a normal direction of the movement path of the head.

3. The behavior detection method according to claim 1, wherein the setting includes setting the stand-up detection line that passes through a midpoint between the lowest point of the forward bending and the position of the head when the person to be detected stands by the bed.

4. The behavior detection method according to claim 1, further comprising:
    stopping, when the position of the head is inside a wake-up line for determining whether the person to be detected is in a recumbent position or a sitting position in the bed area of the image, any of the processing for detecting the motion of bending forward, setting the stand-up detection line, and detecting the stand-up motion.

5. A behavior detection apparatus comprising:
    a processor that executes a process comprising;
    detecting a position of a head from an image;
    detecting, based on the position of the head, a motion of bending forward when a person to be detected sits up in a width direction of a bed in a bed area of the image and stands up from the sitting state;
    when a movement of the head is detected to be forward bending, dynamically setting, based on a movement path of the head, a stand-up detection line for determining bed leaving of the person to be detected between a lowest point of the forward bending and the position of the head when the person to be detected stands by the bed, the stand-up detection line being set in a position not overlapping with a forward bending detection line by which the motion of bending forward is detected; and
    detecting a stand-up motion when the head passes the dynamically set stand-up detection line.

* * * * *